(12) United States Patent
Abolmaesumi et al.

(10) Patent No.: US 11,367,001 B2
(45) Date of Patent: Jun. 21, 2022

(54) NEURAL NETWORK IMAGE ANALYSIS

(71) Applicant: The University of British Columbia, Vancouver (CA)

(72) Inventors: Purang Abolmaesumi, Vancouver (CA); Zhibin Liao, Vancouver (CA); Teresa Tsang, Vancouver (CA); Delaram Behnami, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 17/393,955

(22) Filed: Aug. 4, 2021

(65) Prior Publication Data

US 2021/0365786 A1 Nov. 25, 2021

Related U.S. Application Data

(63) Continuation of application No. PCT/CA2020/050147, filed on Feb. 5, 2020.
(Continued)

(51) Int. Cl.
*G06N 3/08* (2006.01)
*G06K 9/62* (2022.01)
(Continued)

(52) U.S. Cl.
CPC .............. *G06N 3/08* (2013.01); *G06K 9/6257* (2013.01); *G06N 3/0445* (2013.01);
(Continued)

(58) Field of Classification Search
CPC ......... G06T 7/0012; G06T 2207/30048; G06T 7/0014; G06T 2207/10016;
(Continued)

(56) References Cited

U.S. PATENT DOCUMENTS 8,175,362 B2 5/2012 Sathyanarayana
9,955,876 B2 5/2018 Chirife
(Continued)

OTHER PUBLICATIONS

Abdi, Amir H., et al.; "Automatic quality assessment of echocardiograms using convolutional neural networks Feasibility on the apical four-chamber view," IEEE TMI, vol. 36, No. 6, pp. 1221-1230, 2017.
(Continued)

*Primary Examiner* — Nay A Maung
*Assistant Examiner* — Jose M Torres
(74) *Attorney, Agent, or Firm* — Kolitch Romano LLP

(57) ABSTRACT

A computer-implemented method of facilitating neural network image analysis involves receiving signals representing a set of images, causing at least one neural network function to be applied to the set of images to determine at least one property confidence distribution parameter, and causing a cumulative distribution function defined at least in part by the at least one property confidence distribution parameter to be applied to a plurality of ranges, each range associated with a respective property that may be associated with the set of images, to determine a plurality of property confidences, each of the property confidences representing a confidence that the set of images should be associated with a respective one of the properties. Other methods, systems, and computer-readable media are disclosed.

21 Claims, 26 Drawing Sheets

Related U.S. Application Data

(60) Provisional application No. 62/894,099, filed on Aug. 30, 2019, provisional application No. 62/801,827, filed on Feb. 6, 2019.

(51) Int. Cl.
  *G06T 7/00* (2017.01)
  *G16H 30/40* (2018.01)
  *G16H 50/20* (2018.01)
  *G06N 3/04* (2006.01)

(52) U.S. Cl.
  CPC ......... *G06N 3/0481* (2013.01); *G06T 7/0012* (2013.01); *G16H 30/40* (2018.01); *G16H 50/20* (2018.01); *G06T 2207/20081* (2013.01); *G06T 2207/20084* (2013.01); *G06T 2207/30048* (2013.01)

(58) Field of Classification Search
  CPC . G06T 2207/10132; G06T 2207/20081; G06T 2207/20084; G06K 9/6257; G06N 3/08; G06N 3/0445; G06N 3/0454; G06N 3/0481; G16H 30/40; G16H 50/20; G06V 10/7747; G06V 30/19147
  See application file for complete search history.

(56) References Cited

U.S. PATENT DOCUMENTS

| | | | |
|---|---|---|---|
| 9,962,087 B2 | 5/2018 | Garnavi et al. | |
| 10,631,828 B1* | 4/2020 | Hare, II | A61B 8/466 |
| 2018/0192987 A1 | 7/2018 | Salgo et al. | |
| 2019/0104949 A1 | 4/2019 | Cadieu et al. | |

OTHER PUBLICATIONS

Abdi, Amir H., et al.; "Quality assessment of echocardiographic cine using recurrent neural networks: Feasibility on five standard view planes," in MICCAI. Springer, pp. 302-310, 2017.
Bartlett, Peter L., et al.; "Convexity, classification, and risk bounds," Journal of the American Statistical Association, vol. 101, No. 473, pp. 138-156, 2006.
Behnami, Delaram, et al.; "Automatic detection of patients with a high risk of systolic cardiac failure in echocardiography," Deep Learning in Medical Image Analysis and Multimodal Learning for Clinical Decision Support, pp. 65-73. Springer, 2018.
Beigman, Eyal, et al.; "Learning with annotation noise," in Joint Conf of the 47th Annual Meeting of the ACL and the 4th Int. Joint Conf. on NLP of the AFNLP:, vol. 1. ACL, pp. 280-287, 2009.
Blundell, Charles, et al.; "Weight uncertainty in neural networks," in ICML, pp. 1613-1622, 2015.
Brennan P., et al.; "Statistical methods for assessing observer variability in clinical measures," BMJ, vol. 304, No. 6840, p. 1491, 1992.
Brodley, Carla E., et al.; "Identifying mislabeled training data," JAIR, vol. 11, pp. 131-167, 1999.
Chatelain, Pierre; "Confidence-driven control of an ultrasound probe: Target-specific acoustic window optimization," in IEEE ICRA, pp. 3441-3446, 2016.
Denker John S., et al.; "Transforming neural-net output levels to probability distributions," NIPS, pp. 853-859, 1991.
Der Kiureghian, Armen, et al.; "Aleatory or epistemic? does it matter?" Structural Safety, vol. 31, No. 2, pp. 105-112, 2009.
El-Zehiry, Noha, et al.; "Learning the manifold of quality ultrasound acquisition," in MICCAL Springer, pp. 122-130, 2013.
Foley, Thomas A., et al.; "Measuring left ventricular ejection fraction-techniques and po¬tential pitfalls," European Cardiology 8(2), 108-114, 2012.
Frenay, Benoit, et al.; "Classification in the presence of label noise: a survey," IEEE Trans. NNLS, vol. 25, No. 5, pp. 845-869, 2014.
Gal, Yarin, et al.; "Dropout as a bayesian approximation: Representing model uncertainty in deep learning," in ICML, pp. 1050-1059, 2015.
Gal, Yarin; "Uncertainty in Deep Learning" from the Dissertation for the degree of Doctor of Philosophy, Gonville and Caius College, 2016. URL: http://mlg.eng.cam.ac.uk/yarin/thesis/thesis.pdf.
Gal, Yarin, et al.; "Bayesian convolutional neural networks with bernoulli approximate variational inference," ICLR Workshop, 2016.
Graves, Alex; "Practical variational inference for neural networks," in NIPS, pp. 2348-2356, 2011.
Gu, Bin, et al.; "Sparse regression with output correlation for cardiac ejection fraction estimation," Information Sciences 423, 303-312, 2018.
Guo, Chuan, et al.; "On calibration of modern neural networks," in ICML, pp. 1321-1330, 2017.
Hinton, Geoffrey, et al.; "Distilling the knowledge in a neural network," in NIPS Deep Learning and Representation Learning Workshop, 2015.
Hochreiter Sepp, et al.; "Long short-term memory," Neural Computation, vol. 9, No. 8, pp. 1735-1780, 1997.
Huang, Sheng-Wen, et al., "Detection and display of acoustic window for guiding and training cardiac ultrasound users," in SPIE Medical Imaging, vol. 9040. ISOP, pp. 1-7, 2014.
Huang, Gao, et al.; "Densely connected convolutional networks," in IEEE CVPR, vol. 1-2, p. 3, 2017.
Ioffe, Sergey, et al.; "Batch normalization: Accelerating deep network training by reducing internal covariate shift," in ICML, pp. 448-456, 2015.
Jafari, Mohammad H., et al.; "A unified framework integrating recurrent fully-convolutional networks and optical flow for segmentation of the left ventricle in echocardiography data," Deep Learning in Medical Image Analysis and Multimodal Learning for Clinical Decision Support, pp. 29-37. Springer, 2018.
Kabani, AbdulWahab, et al.; "Ejection fraction estimation using a wide convolutional neural network," Image Analysis and Recognition, pp. 87-96. Springer, 2017.
Kendall, Alex, et al.; "What uncertainties do we need in bayesian deep learning for computer vision?" in NIPS, pp. 5574-5584, 2017.
Kingma, Diederik P., et al.; "Adam: A method for stochastic optimization," in ICLR, pp. 1-15, 2015.
Leclerc, Sarah, et al.; "A fully automatic and multi-structural segmentation of the left ventricle and the myocardium on highly heterogeneous 2D echocardiographic data," Ultrasonics Symposium (IUS), 2017 IEEE Internan¬tional, pp. 1-4. IEEE, 2017.
Leibig, Christian, et al.; "Leveraging uncertainty information from deep neural networks for disease detection," Scientific Reports, vol. 7, No. 1, p. 17816, 2017.
Loizou, C. P., et al.; "Quality evaluation of ultrasound imaging in the carotid artery based on normalization and speckle reduction filtering," MBEC, vol. 44, No. 5, p. 414, 2006.
Mackay, David J. C.; "A practical bayesian framework for backpropagation networks," Neural Computation, vol. 4, No. 3, pp. 448-472, 1992.
Miranda, Andre L., et al.; "Use of classification algorithms in noise detection and elimination," in Int. Conf. HAIS. Springer, pp. 417-424, 2009.
Nair, Tanya, et al.; "Exploring uncertainty measures in deep networks for multiple sclerosis lesion detection and segmentation," in MICCAI. Springer, pp. 655-663, 2018.
Nair, Vinod, et al.; "Rectified linear units improve restricted boltzmann machines," in ICML, pp. 807-814, 2010.
Neal, Radford M.; "Bayesian learning for neural networks," Springer Science & Business Media, vol. 118, 2012.
Perez, C. J., et al.; "Misclassified multinomial data: a bayesian approach." RACSAM, vol. 101, No. 1, pp. 71-80, 2007.
Potter, Elizabeth, et al.; "Assessment of left ventricular function by echocardiog¬raphy: the case for routinely adding global longitudinal strain to ejection fraction," JACC: Cardiovascular Imaging 11(2), 260-274, 2018.
Romero Adriana, et al.; "Fitnets: Hints for thin deep nets," ICLR, 2014.

(56) References Cited

OTHER PUBLICATIONS

Silva, Joao F., et al.; "Ejection fraction classification in transthoracic echocardiography using a deep learning approach," CBMS, pp. 123-128. IEEE, 2018.

Smistad, Erik, et al.; "2D left ventricle segmentation using deep learning," Ultrasonics, pp. 1-4. IEEE, 2017.

Srivastava Nitish, et al.; "Dropout: A simple way to prevent neural networks from overfitting," JMLR, vol. 15, No. 1, pp. 1929-1958, 2014.

Tan, Li K., et al.; "Cardiac left ventricle segmentation using convolutional neural network regression," Biomedical Engineering and Sciences (IECBES), 2016 IEEE EMBS Conference, pp. 490-493. IEEE, 2016.

Tomczack, Agnieszka, et al.; "Learn to estimate labels uncertainty for quality assurance," arXiv preprint arXiv:1909.08058, 2019.

Tran, Du, et al.; "A closer look at spatiotemporal convolutions for action recognition," CVPR, pp. 6450-6459, 2018.

Tsantis, Starvos, et al.; "Multiresolution edge detection using enhanced fuzzy c-means clustering for ultrasound image speckle reduction," Medical Physics, vol. 41, No. 7, pp. 72903-1-11, 2014.

Van Rikxoort, Eva M., et al.; "Automated segmentation of pulmonary structures in thoracic computed tomography scans: a review," Physics in Med & Bio., vol. 58, No. 17, p. 187, 2013.

Vaseli, Hooman, et al.; "Designing lightweight deep learning models for echocardiography view classification," Medical Imaging 2019: Image=Guided Procedures, Robotic Interventions, and Modeling, vol. 10951, p. 109510F. International Society for Optics and Photonics, 2019.

Wu, Lingyun, et al.; "FUIQA: Fetal ultrasound image quality assessment with deep convolutional networks," IEEE Trans. Cyber., vol. 47, No. 5, pp. 1336-1349, 2017.

Ribiero, Ricardo T. et al., "An Ultrasound-Based Computer-Aided Diagnosis Tool for Steatosis Detection," IEEE Journal of Biomedical and Health Informatics, Jul. 2014, vol. 18, No. 4, pp. 1397-1403.

Canadian Intellectual Property Office, International Search Report and Written Opinion of the International Searching Authority, dated Apr. 16, 2020, in PCT/CA2020/050147 which is the international application which shares the same priority as this U.S. application.

Nix, D. A. et al.; "Estimating the mean and variance of the target probability distribution," Proceedings of 1994 IEEE International Conference on Neural Networks, pp. 55-60 vol. 1, doi: 10.1109/ICNN.1994.374138, 1994.

World Health Organization; Global health observatory (gho) data, retrieved from Web.Archive.org, 2017. URL: https://web.archive.org/web/20170713121552/http://www.who.int/gho/mortality_burden_disease/causes_death/top_10/en/.

Xue, Wufeng, et al.; "Full quantification of left ventricle via deep multitask learning network respecting intra-and inter-task relatedness," MICCAI, pp. 276-284, Springer, 2017.

Zadeh, Lotfi A., et al.; "Toward a theory of fuzzy information granulation and its centrality in human reasoning and fuzzy logic," Fuzzy Sets and Systems, vol. 90, No. 2, pp. 111-127, 1997.

Zhang, Jeffrey, et al.; "A web-deployed computer vision pipeline for automated determination of cardiac structure and function and detection of disease by two-dimensional echocardiography," arXiv:1706.07342, 2017.

Zhuang, Xiahai, et al.; "Evaluation of algorithms for multi- modality whole heart segmentation: An open-access grand challenge," arXiv preprint arXiv:1902.07880, 2019.

* cited by examiner

500

Property Confidence Record

| | | |
|---|---|---|
| 502 — | Property 1 | Poor |
| 504 — | Confidence | 0 |
| 506 — | Property 2 | Fair |
| 508 — | Confidence | 0.01 |
| 510 — | Property 3 | Good |
| 512 — | Confidence | 0.83 |
| 514 — | Property 4 | Excellent |
| 516 — | Confidence | 0.16 |

1000

Ultrasound Session Training Record

1002 — Session ID      1
1004 { Image 1      ...
       Image 2      ...
       Image 3      ...
       ...
1006 — Quality assessment      Good

1020

Training Confidence Record

1022 — Session ID      1
1024 — Confidence     0.83

Property Confidence Record

| | | |
|---|---|---|
| 1542 — | Property 1 | Severe dysfunction |
| 1544 — | Confidence | 0 |
| 1546 — | Property 2 | Moderate dysfunction |
| 1548 — | Confidence | 0.05 |
| 1550 — | Property 3 | Mild dysfunction |
| 1552 — | Confidence | 0.80 |
| 1554 — | Property 4 | Normal function |
| 1556 — | Confidence | 0.15 |

Training Confidence Record

2042 — Session ID     1
2044 — Confidence     0.58

FIG. 24

NEURAL NETWORK IMAGE ANALYSIS

CROSS-REFERENCES

The following applications and materials are incorporated herein, in their entireties, for all purposes: U.S. Provisional Application No. 62/801,827 entitled "DETERMINING A CONFIDENCE INTERVAL IN ULTRASOUND IMAGE ASSESSMENT", filed on Feb. 6, 2019, and U.S. Provisional Application No. 62/894,099, which was assigned a title of "DUAL-VIEW JOINT ESTIMATION OF LEFT VENTRICULAR EJECTION FRACTION WITH UNCERTAINTY MODELLING IN ECHOCARDIOGRAMS", filed on Aug. 30, 2019. However, such material is only incorporated to the extent that no conflict exists between the incorporated material and the statements and drawings set forth herein. In the event of any such conflict, including any conflict in terminology, the present disclosure is controlling

FIELD

Embodiments relate to neural network image analysis and more particularly to computer implemented neural network image analysis using at least one cumulative distribution function.

INTRODUCTION

Although computer-implemented deep learning or neural network classifier systems are powerful modelling tools, direct mapping from images to expert labels can be difficult due to observer variability. In clinical studies, for example, a lack of consistency in diagnostic judgment and decision making may result in neural network classifier systems that are less accurate and/or provide inconsistent or unpredictable results. For example, inconsistency may result from an unknown standard and/or from observer interpretation of partial information. Some known computer classifying neural network systems try to compensate for observer variability using data cleaning methods to try to identify and clean noise samples before training a classifier, but hard informative samples may also be removed as they can be confused with random noise. Accordingly, some known computer classifying neural network systems do not work well in high-noise ratio problems, such as, for example, as is present in some clinical data.

SUMMARY

The present disclosure provides systems, apparatuses, and methods relating to computer implemented facilitation of neural network image analysis.

In accordance with various embodiments, there is provided a computer-implemented method of facilitating neural network image analysis, the method involving receiving signals representing a set of images, causing at least one neural network function to be applied to the set of images to determine at least one property confidence distribution parameter, and causing a cumulative distribution function defined at least in part by the at least one property confidence distribution parameter to be applied to a plurality of ranges, each range associated with a respective property that may be associated with the set of images, to determine a plurality of property confidences, each of the property confidences representing a confidence that the set of images should be associated with a respective one of the properties.

The cumulative distribution function may include a Gaussian cumulative distribution function and the at least one property confidence distribution parameter may include a property distribution mean and a property distribution standard deviation.

The cumulative distribution function may include a Laplace cumulative distribution function and the at least one property confidence distribution parameter may include a location and scale parameter for the Laplace cumulative distribution function.

The set of images may include ultrasound images.

The properties may include at least one clinical parameter related to a subject depicted by the set of images.

The properties may include echocardiogram estimated ejection fraction function diagnoses.

The properties may include a quality assessment of the set of images.

The method may involve producing signals for causing at least one display to display a representation of at least one of the property confidences.

The method may involve producing signals for causing at least one display to display a representation of the at least one property confidence distribution parameter.

The method may involve training the at least one neural network function, the training involving receiving signals representing a plurality of sets of training images, receiving signals representing expert evaluation properties, each of the expert evaluation properties provided by an expert and associated with one of the sets of training images, and causing the at least one neural network function to be trained using the sets of training images as respective inputs, wherein causing the at least one neural network function to be trained involves, for each of the sets of training images, causing the at least one neural network function to be applied to the set of training images to determine at least one training property confidence distribution parameter, and causing a training cumulative distribution function defined at least in part by the at least one training property confidence distribution parameter to be applied to a range associated with the expert evaluation property associated with the set of images, to determine a training property confidence representing a confidence that the set of training images should be associated with the expert evaluation property. The method may involve causing the at least one neural network function to be updated to reduce a loss, the loss determined based at least in part on the determined training property confidences.

In accordance with various embodiments, there is provided a computer-implemented method of training at least one neural network function to facilitate image analysis, the method involving receiving signals representing a plurality of sets of training images, receiving signals representing expert evaluation properties, each of the expert evaluation properties provided by an expert and associated with one of the sets of training images, and causing the at least one neural network function to be trained using the sets of training images as respective inputs, wherein causing the at least one neural network function to be trained involves, for each of the sets of training images, causing the at least one neural network function to be applied to the set of training images to determine at least one property confidence distribution parameter, and causing a cumulative distribution function defined at least in part by the at least one property confidence distribution parameter to be applied to a range associated with the expert evaluation property associated with the set of images, to determine a property confidence representing a confidence that the set of training images should be associated with the expert evaluation property. The method may involve causing the at least one neural network function to be updated to reduce a loss, the loss determined based at least in part on the determined property confidences.

The cumulative distribution function may include a Gaussian cumulative distribution function and the at least one property confidence distribution parameter may include a property distribution mean and a property distribution standard deviation.

The cumulative distribution function may include a Laplace cumulative distribution function and the at least one property confidence distribution parameter may include a location and scale parameter for the Laplace cumulative distribution function.

The set of images may include ultrasound images.

The properties may include at least one clinical parameter related to a subject depicted by the set of images.

The properties may include echocardiogram estimated ejection fraction function diagnoses.

The properties may include a quality assessment of the set of images.

In accordance with various embodiments, there is provided a system for facilitating ultrasonic image analysis including at least one processor configured to perform any of the above methods.

In accordance with various embodiments, there is provided a non-transitory computer readable medium having stored thereon codes which when executed by at least one processor cause the at least one processor to perform any of the above methods.

In accordance with various embodiments, there is provided a system for facilitating neural network image analysis, the system including means for receiving signals representing a set of images, means for causing at least one neural network function to be applied to the set of images to determine at least one property confidence distribution parameter, and means for causing a cumulative distribution function defined at least in part by the at least one property confidence distribution parameter to be applied to a plurality of ranges, each range associated with a respective property that may be associated with the set of images, to determine a plurality of property confidences, each of the property confidences representing a confidence that the set of images should be associated with a respective one of the properties.

In accordance with various embodiments, there is provided a system for training at least one neural network function to facilitate image analysis, the system including means for receiving signals representing a plurality of sets of training images, means for receiving signals representing expert evaluation properties, each of the expert evaluation properties provided by an expert and associated with one of the sets of training images, and means for causing the at least one neural network function to be trained using the sets of training images as respective inputs, wherein the means for causing the at least one neural network function to be trained includes means for, for each of the sets of training images, causing the at least one neural network function to be applied to the set of training images to determine at least one property confidence distribution parameter, and causing a cumulative distribution function defined at least in part by the at least one property confidence distribution parameter to be applied to a range associated with the expert evaluation property associated with the set of images, to determine a property confidence representing a confidence that the set of training images should be associated with the expert evaluation property. The system may include means for causing the at least one neural network function to be updated to reduce a loss, the loss determined based at least in part on the determined property confidences.

Features, functions, and advantages may be achieved independently in various embodiments of the present disclosure, or may be combined in yet other embodiments, further details of which can be seen with reference to the following description and drawings.

BRIEF DESCRIPTION OF THE DRAWINGS

In drawings which illustrate embodiments of the present disclosure,

FIG. 16 is a representation of an exemplary training confidence record that may be used in the system shown in FIG. 11 in accordance with various embodiments of the present disclosure;

FIG. 20 is a representation of an exemplary property confidence record that may be used in the system shown in FIG. 11 in accordance with various embodiments of the present disclosure;

FIG. 24 is a representation of an exemplary training confidence record that may be used by the neural network trainer shown in FIG. 21 in accordance with various embodiments of the present disclosure;

DETAILED DESCRIPTION

Variability in expert labelling, such as clinical labelling, may come from two sources: 1) the lack of consistency within an observer (i.e., intra-observer variability), and 2) the lack of consistency among observers (i.e., inter-observer variability). In machine learning, uncertainty or noise may be categorized as aleatoric uncertainty, which is the observer variability noise that is inherent in the observations, or epistemic uncertainty, which is the uncertainty or noise that is introduced by the learning model. Epistemic uncertainty may be explained away given enough data; thus it is also known as model uncertainty. Several Bayesian inference approaches and more recent Bayesian neural networks (BNN) are designed to address the uncertainty in the induced classifier by imposing a prior distribution over model parameters. Nevertheless, the Bayesian methods usually have a low convergence rate, which may not be suitable for solving large-scale problems.

Some embodiments described herein aim to solve a regression problem where only categorical expert labels are provided. In various embodiments, a computer system employing a Cumulative Density Function Probability (CDF-Prob) solution is provided, which may address observer variability as aleatoric uncertainty. In some embodiments, the CDF-Prob solution may model experts' opinions using a cumulative distribution or density function, such as a Laplace or Gaussian distributions over the regression space, for example.

In various embodiments, the computer systems described herein may be effective in various fields where labels are categorical (i.e., degrees of pathology severity), and subject to large observer variability in gold standard labels, such as, in the context of clinical labeling including, for example, echo quality assessment and/or echo based ejection fraction assessment. In various embodiments, the systems described herein and the use thereof may improve compatibility of neural network function based analysis with the use of categorical labels and/or may improve the classification performance therefor.

Figure 1:
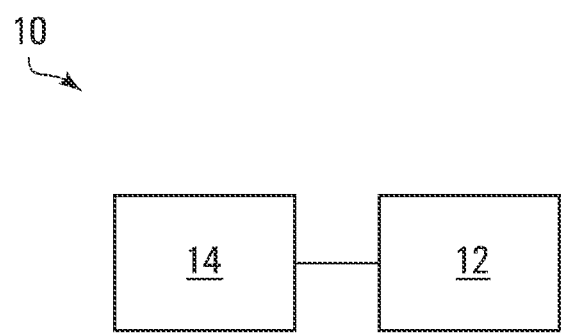
FIG. 1 is a schematic view of a system for facilitating neural network image analysis functions according to various embodiments of the present disclosure.

Referring to FIG. 1, there is shown a schematic drawing of the general elements that may be included in a system 10 for facilitating neural network image analysis, in accordance with various embodiments. The system 10 includes a computer-implemented image analyzer 12 in communication with an image data source 14.

In various embodiments, the system 10 may be configured to cause a set of images to be analyzed and property confidences to be determined, with each property confidence representing a confidence that the set of images should be associated with a respective one of a plurality of properties. For example, in some embodiments, the system 10 may be configured to cause a set of ultrasound images to be analyzed to determine property confidences relating to quality assessment of the ultrasound images.

In various embodiments, the system 10 may facilitate better understanding of the quality of ultrasound images being acquired and this may help facilitate improved acquisition of quality ultrasound images by operators of ultrasound image acquisition systems. In various embodiments, this may be particularly helpful given that 2D echocardiography (echo) is the primary point-of-care imaging modality for early diagnosis of cardiovascular disease, since it is inexpensive, non-invasive, and widely available.

Figure 2:
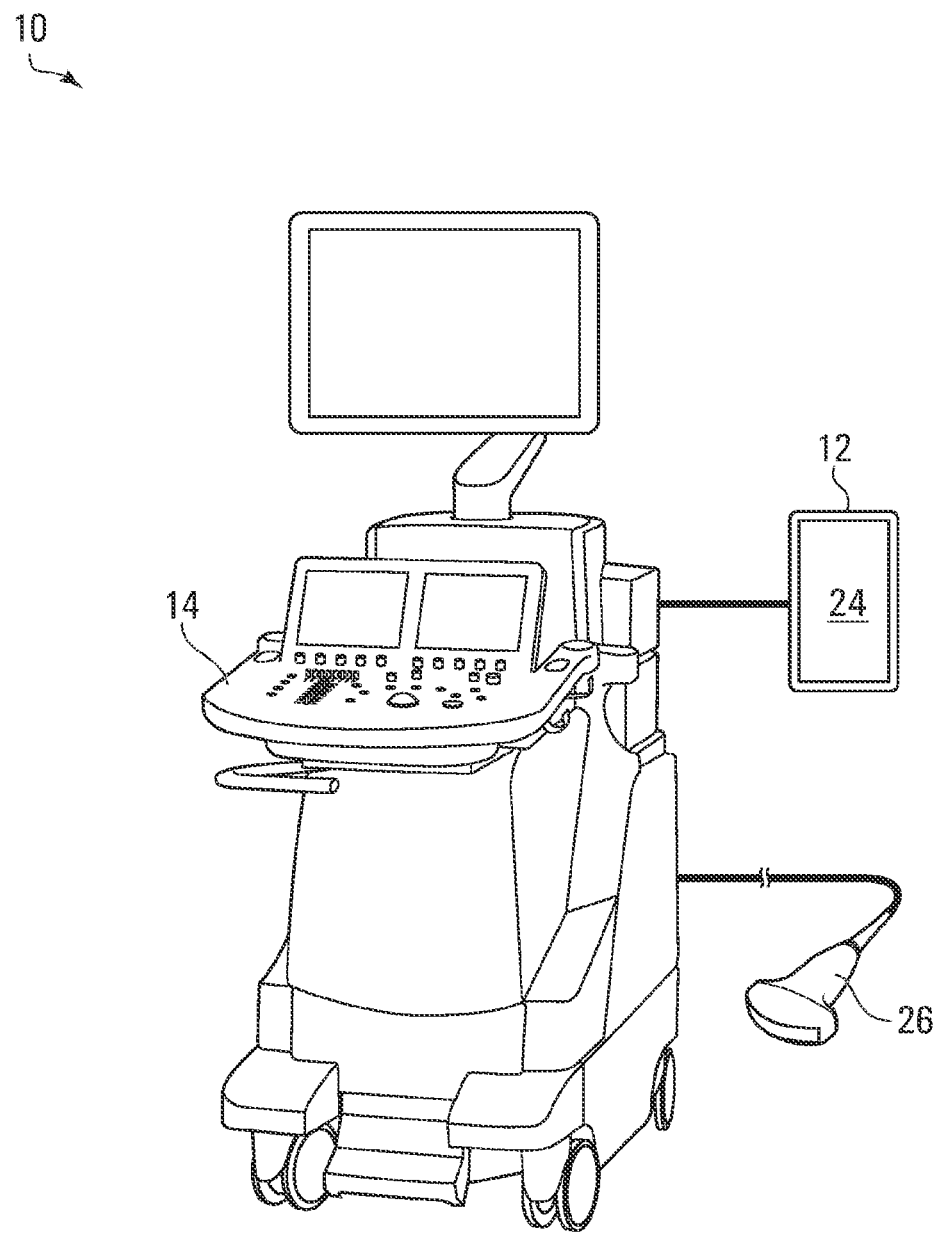
FIG. 2 is a schematic view of the system shown in FIG. 1 according to various embodiments of the present disclosure.

Referring to FIG. 2, there is shown an implementation of the system 10 shown in FIG. 1 in accordance with various embodiments. Referring to FIG. 2, the system 10 includes an ultrasound machine acting as the image data source 14 and a mobile device acting as the image analyzer 12. In various embodiments, the mobile device may include a display 24 and the ultrasound machine may include a transducer 26.

In various embodiments, the system 10 may be configured to provide to users of an ultrasound machine, real-time or near real-time feedback of the quality of the images being captured. In some embodiments, a quality assessment may represent an assessment of suitability of the received set of ultrasound images for quantified clinical measurement of anatomical features. In some embodiments, this may help the users to obtain higher quality images when operating the ultrasound machine. For example, in some embodiments, the system 10 may be configured to determine four confidences or confidence values associated with quality assessments of "Poor", "Fair", "Good", or "Excellent", respectively, and to display a representation of the determined confidences to the user. In various embodiments, these confidences may represent aleatoric confidences or a combination of aleatoric and epistemic confidences, and thus reflecting a potential for inconsistent labeling by an expert, rather than merely epistemic confidences. In various embodiments, displaying the confidences may be particularly useful to a user of the ultrasound machine to determine how much they should rely on the displayed quality assessment determinations. In various embodiments, this may allow operators to more easily recognize specific features and structures required of various ultrasound images and/or views and thus the system 10 may be able to facilitate the capture of diagnostically relevant sets of ultrasound images or heart cine series.

Referring to FIG. 2, the ultrasound machine acting as the image data source 14 may be controlled by a user or operator to send and receive ultrasound signals to and from a subject via the transducer 26, to produce ultrasound image representations of the subject. For example, in some embodiments, the subject may be a person or patient. In some embodiments, the transducer 20 may be manipulated such that the ultrasound machine acting as the image data source 14 produces a set of ultrasound images of a heart of the person, for example.

In some embodiments, a representation of the set of ultrasound images may be transmitted to the image analyzer 12. In some embodiments, the system 10 may include a frame grabber configured to capture raw video output from the ultrasound machine and to transmit a serial data stream representing a set of ultrasound images to the image analyzer 12. For example, in some embodiments, the frame grabber may be configured to receive its input directly from an imaging output port of the ultrasound machine, using an Epiphan AV.IO frame grabber, for example, to capture and convert the raw video output to a serial data stream. In some embodiments, the frame grabber output may be adapted from USB-A to USB-C with an On-The-Go (OTG) adapter, allowing the frame grabber to pipe video output from the ultrasound machine directly into the image analyzer 12. As described below, the image analyzer 12 may run or implement a neural network which is configured to process the video output received from the frame grabber. In some embodiments, the image analyzer 12 may use TensorFlow Java inference interface, for example.

In some embodiments, the image analyzer 12 may be configured to receive signals representing a set of images. For example, in some embodiments, the image analyzer 12 may be configured to receive the ultrasound images generated by the ultrasound machine acting as the image data source 14 as shown in FIG. 2.

In some embodiments, the set of images received may represent a video or cine series and may be a temporally ordered set of images. In some embodiments, the set of images received may represent an echocardiographic cine series, for example, showing a patient's heart over time.

The image analyzer 12 may then cause at least one neural network function to be applied to the set of images to determine at least one property confidence distribution parameter. For example, in some embodiments a quality assessment mean and standard deviation neural network function may be stored in the image analyzer 12. The quality assessment mean and standard deviation neural network function may be configured to take as an input a set of ultrasonic images and to output mean and standard deviation values, which define a Gaussian probability density or distribution function. The mean and standard deviation values may act as property confidence distribution parameters. In various embodiments, the Gaussian probability density function may be used to determine probabilities of various numerical quality assessments for the set of ultrasonic images. For example, the numerical quality assessments may vary from 0 representing very poor quality to 1 representing very high quality.

The image analyzer 12 may then cause a cumulative distribution or density function defined at least in part by the at least one property confidence distribution parameter to be applied to a plurality of ranges, each range associated with a respective property that may be associated with the set of images, to determine a plurality of property confidences, each of the property confidences representing a confidence that the set of images should be associated with a respective one of the properties. In some embodiments, the cumulative distribution function may be a Gaussian cumulative distribution function defined by the mean and standard deviation values previously determined by the image analyzer 12.

In some embodiments, respective ranges of numerical quality assessments may be associated with or assigned to respective quality assessments or quality assessment categories. For example, numerical quality assessments between 0 and 0.25 may be associated with a quality assessment category of "Poor", numerical quality assessments between 0.25 and 0.5 may be associated with a quality assessment category of "Fair", numerical quality assessments between 0.5 and 0.75 may be associated with a quality assessment category of "Good", and numerical quality assessments between 0.75 and 1 may be associated with a quality assessment category of "Excellent". In various embodiments, the quality assessment categories may act as properties that may be associated with the set of images.

Accordingly, in some embodiments, the image analyzer 12 may apply the Gaussian cumulative distribution function to each of the ranges, 0-0.25, 0.25-0.5, 0.5-0.75, and 0.75-1, to determine confidences or probabilities for each range. In some embodiments, the image analyzer 12 may normalize the confidences such that they sum to 1.

In some embodiments, by using a cumulative distribution function applied over ranges, the image analyzer 12 may facilitate use with categorical labeling, which may be particularly desirable in various clinical settings. In some embodiments, using a cumulative distribution applied over ranges may facilitate determination of probabilities or confidences rather than probability densities, which may be more easily understood by a user of the system 10.

In some embodiments, the image analyzer 12 may be configured to produce signals for causing the display 24 to display a representation of at least one of the property confidences. For example, in some embodiments, the image analyzer 12 may be configured to produce signals representing the confidences associated with each of the quality assessment categories for causing the display 24 to display a representation of the confidences. In various embodiments, reviewing the confidences in view of the quality assessment categories with which they are associated may provide a user of the system 10 with an understanding of the quality of the images that are being captured.

Image Analyzer—Processor Circuit

Figure 3:
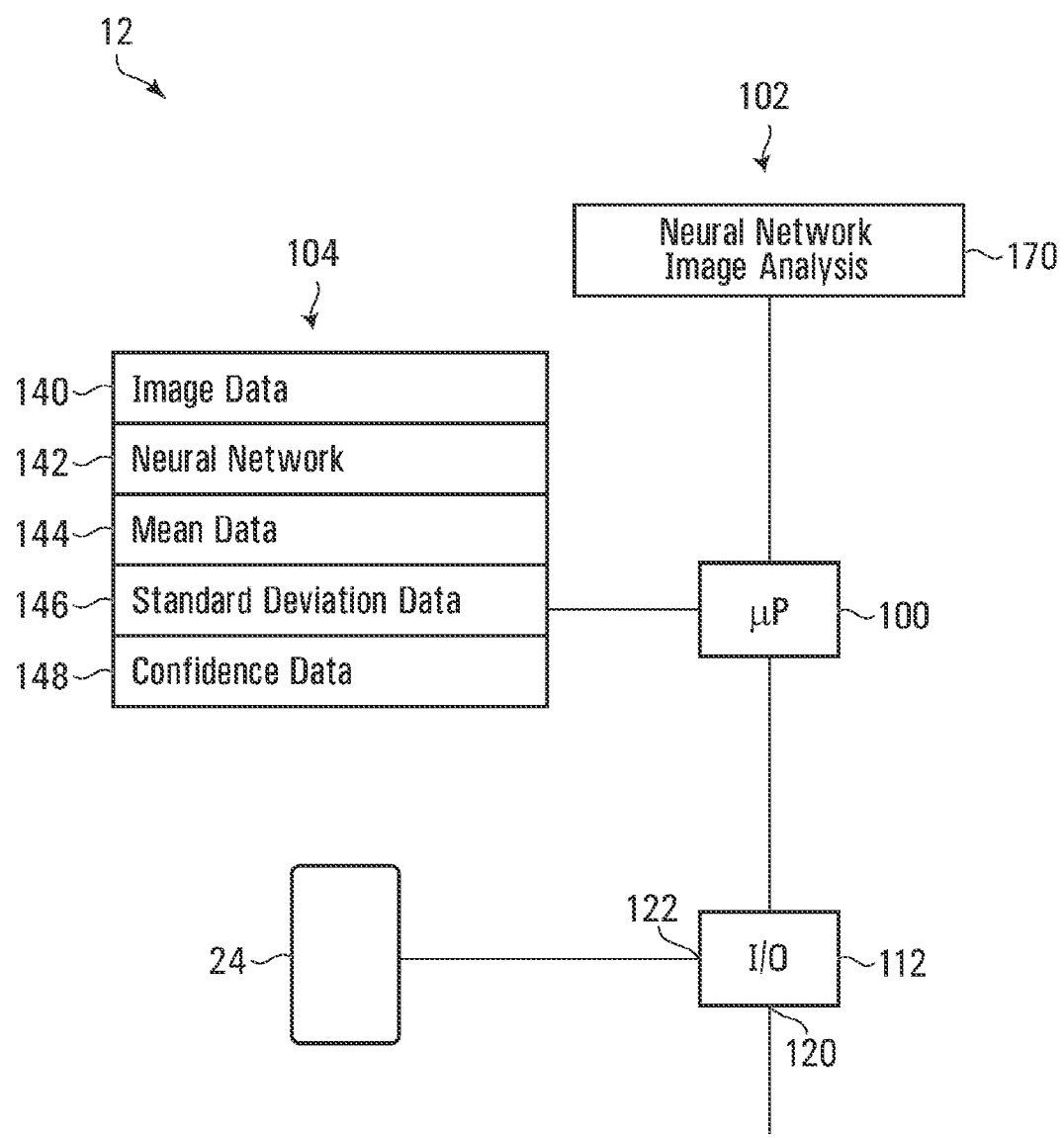
FIG. 3 is a schematic view of an image analyzer of the system shown in FIG. 2 including a processor circuit in accordance with various embodiments of the present disclosure.

Referring now to FIG. 3, a schematic view of the image analyzer 12 of the system 10 shown in FIGS. 1 and 2 according to various embodiments is shown. Referring to FIG. 3, the image analyzer 12 includes a processor circuit including an analyzer processor 100 and a program memory 102, a storage memory 104, and an input/output (I/O)

interface 112, all of which are in communication with the analyzer processor 100. In various embodiments, the analyzer processor 100 may include one or more processing units, such as for example, a central processing unit (CPU), a graphical processing unit (GPU), and/or a field programmable gate array (FPGA). In some embodiments, any or all of the functionality of the image analyzer 12 described herein may be implemented using one or more FPGAs.

The I/O interface 112 includes an interface 120 for communicating with the image data source 14 and an interface 122 for communicating with the display 24. In some embodiments, the I/O interface 112 may also include an additional interface for facilitating networked communication through a network such as the Internet. In some embodiments, any or all of the interfaces of the I/O interface 112 may facilitate a wireless or wired communication. In some embodiments, each of the interfaces shown in FIG. 3 may include one or more interfaces and/or some or all of the interfaces included in the I/O interface 112 may be implemented as combined interfaces or a single interface.

In some embodiments, where a device is described herein as receiving or sending information, it may be understood that the device receives signals representing the information via an interface of the device or produces signals representing the information and transmits the signals to the other device via an interface of the device.

Processor-executable program codes for directing the analyzer processor 100 to carry out various functions are stored in the program memory 102. Referring to FIG. 3, the program memory 102 includes a block of codes 170 for directing the image analyzer 12 to perform facilitating neural network image analysis functions. In this specification, it may be stated that certain encoded entities such as applications or modules perform certain functions. Herein, when an application, module or encoded entity is described as taking an action, as part of, for example, a function or a method, it will be understood that at least one processor (e.g., the analyzer processor 100) is directed to take the action by way of programmable codes or processor-executable codes or instructions defining or forming part of the application.

The storage memory 104 includes a plurality of storage locations including location 140 for storing image data, location 142 for storing neural network data, location 144 for storing mean data, location 146 for storing standard deviation data, and location 148 for storing confidence data. In various embodiments, the plurality of storage locations may be stored in a database in the storage memory 104.

In various embodiments, the block of codes 170 may be integrated into a single block of codes or portions of the block of code 170 may include one or more blocks of code stored in one or more separate locations in the program memory 102. In various embodiments, any or all of the locations 140-148 may be integrated and/or each may include one or more separate locations in the storage memory 104.

Each of the program memory 102 and storage memory 104 may be implemented using one or more storage devices including random access memory (RAM), a hard disk drive (HDD), a solid-state drive (SSD), a network drive, flash memory, a memory stick or card, any other form of non-transitory computer-readable memory or storage medium, and/or a combination thereof. In some embodiments, the program memory 102, the storage memory 104, and/or any portion thereof may be included in a device separate from the image analyzer 12 and in communication with the image analyzer 12 via the I/O interface 112, for example. In some embodiments, the functionality of the analyzer processor 100 and/or the image analyzer 12 as described herein may be implemented using a plurality of processors and/or a plurality of devices, which may be distinct devices which are in communication via respective interfaces and/or a network, such as the Internet, for example.

Image Analyzer Operation

Figure 4:
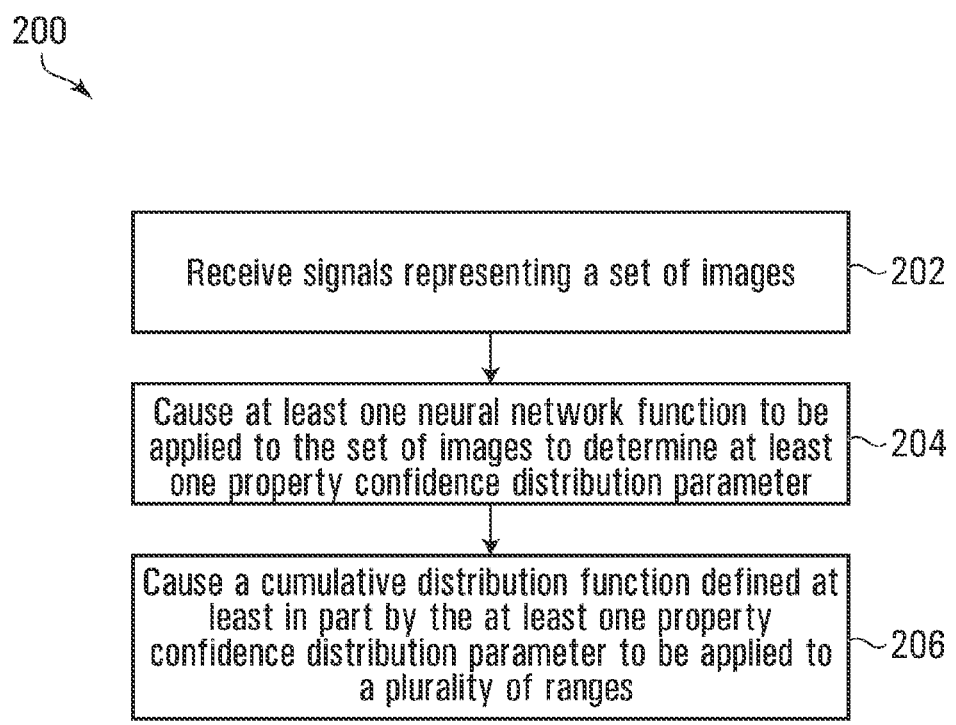
FIG. 4 is a flowchart depicting blocks of code for directing the image analyzer of the system shown in FIG. 2 to perform facilitating neural network image analysis functions in accordance with various embodiments of the present disclosure.

As discussed above, in various embodiments, the image analyzer 12 shown in FIGS. 1-3 may be configured to facilitate neural network image analysis. Referring to FIG. 4, a flowchart depicting blocks of code for directing the analyzer processor 100 shown in FIG. 3 to perform facilitating neural network image analysis functions in accordance with various embodiments is shown generally at 200. The blocks of code included in the flowchart 200 may be encoded in the block of codes 170 of the program memory 102 shown in FIG. 3, for example.

Referring to FIG. 4, the flowchart 200 begins with block 202 which directs the analyzer processor 100 to receive signals representing a set of images. As discussed above, in various embodiments, the image data source 14 may include an ultrasound machine and the image data source 14 and/or a framer grabber may be configured to send to the image analyzer 12 ultrasound images representing the heart of a patient. In some embodiments, block 202 may direct the analyzer processor 100 to receive the ultrasound images from the image data source 14 and to store the received ultrasound images in the location 140 of the storage memory 104 shown in FIG. 3.

In some embodiments, the set of ultrasound images may be a temporally ordered set of ultrasound images representing a video or cine series for a subject. In some embodiments, the subject may be the heart of a patient and the ultrasound images may be referred as an echocine series. Each image of the ultrasound images may be referred to herein as a frame.

In some embodiments, block 202 may direct the analyzer processor 100 to pre-process raw ultrasound images received from the image data source 14 and/or to select a subset of the ultrasound images received from image data source 14 as the set of images to be analyzed. For example, in some embodiments, block 202 may direct the analyzer processor 100 to receive raw ultrasound images at a resolution of 640×480 at 30 Hz. Block 202 may direct the analyzer processor 100 to crop the raw frames down to include only the ultrasound beam, the boundaries of which may be adjustable by the user. The cropped data may be resized down to 120×120 to match input dimensions of the neural network implemented by the image analyzer 12. In some embodiments, block 202 may direct the analyzer processor 100 to perform a simple contrast enhancement step to mitigate quality degradation introduced by the frame grabber.

In some embodiments, block 202 may direct the analyzer processor 100 to store a subset of the received ultrasound images in the location 140 of the storage memory 104. For example, in some embodiments, block 202 may direct the analyzer processor 100 to store ten 120×120 ultrasound images in the location 140 of the storage memory 104 and those ten ultrasound images may act as the received set of ultrasound images. In some embodiments, block 202 may direct the analyzer processor 100 to store the most recent ultrasound images in the location 140 of the storage memory 104. In some embodiments, a copy of the full-resolution data may also be stored in the storage memory 104 for later expert evaluation.

Referring to FIG. 4, after block 202 has been executed, the flowchart continues to block 204. Block 204 directs the analyzer processor 100 to cause at least one neural network function to be applied to the set of images to determine at least one property confidence distribution parameter. In some embodiments, parameters defining a quality assessment mean and standard deviation neural network function may be stored in the location 142 of the storage memory 104 and block 204 may direct the analyzer processor 100 to read the parameters from the location 142 of the storage memory 104 and apply the quality assessment mean and standard deviation neural network function to ten ultrasound images stored in the location 140 of the storage memory 104. For example, a depiction of the quality assessment mean and standard deviation neural network function as applied to a subset 302 of a cine series of ultrasound images, in accordance with various embodiments, is shown at 300 in FIG. 5.

In various embodiments, the quality assessment mean and standard deviation neural network function 300 may include commonly defined first feature extracting neural networks (e.g., 304, 306, and 308), which may include convolutional neural networks. For example, in some embodiments, each of the neural networks 304, 306, and 308 may be implemented as a seven-layer DenseNet model as described in Huang, G., Liu, Z., Weinberger, K. Q., van der Maaten, L.: Densely connected convolutional networks. In: IEEE CVPR. vol. 1-2, p. 3 (2017). In some embodiments, the DenseNet model implementing the commonly defined first feature extracting neural networks 304, 306, and 308 may use the following hyper-parameters. First, the DenseNet may have one convolution layer with sixteen 3×3 filters, which turns gray-scale (1-channel) input images to sixteen channels. Then, the DenseNet may stack three dense blocks, each followed by a dropout layer and an average-pooling layer with filter size of 2×2. In various embodiments, after the third dense block, the average-pooling layer may be applied before the dropout layer. Each dense block may have exactly one dense-layer, which may include a sequence of batch-normalization layer (as per Ioffe, S., Szegedy, C.: Batch normalization: Accelerating deep network training by reducing internal covariate shift. In: Proceedings of the 32nd International Conference on Machine Learning. pp. 448-456. ICML'15, JMLR (2015), for example), a Rectified Linear layer (ReLU) (as per Nair, V., Hinton, G. E.: Rectified linear units improve restricted Boltzmann machines. In: Proceedings of the 27th international conference on machine learning (ICML-10). pp. 807-814 (2010), for example), a 2D convolution layer with 3×3 filters, a dropout layer, a concatenation layer, another 2D convolution layer, another dropout layer, and an average pooling layer.

A batch normalization layer may first normalize the input features by the mean and standard deviation of the features themselves. For each channel (the second dimension) of input, the features from all training samples within a mini-batch may be jointly used to compute the mean and standard deviation values, hence the name batch normalization. After the normalization, the features may be rescaled and shifted by a linear transformation operation. A ReLU activation layer may be used to provide a non-linear transformation to the features. The ReLU activation function is noted as:

$$ReLU(x)=\max(0,x),$$

where x denotes any single element of the input feature vector. A concatenation layer may concatenate features at a given dimension, where in this case, the features may be concatenated at the channel (the second) dimension. A dropout layer may omit a percentage of feature values according to a given value between 0 and 1, which is a regularization technique to reduce overfitting towards the training data.

Figure 6:
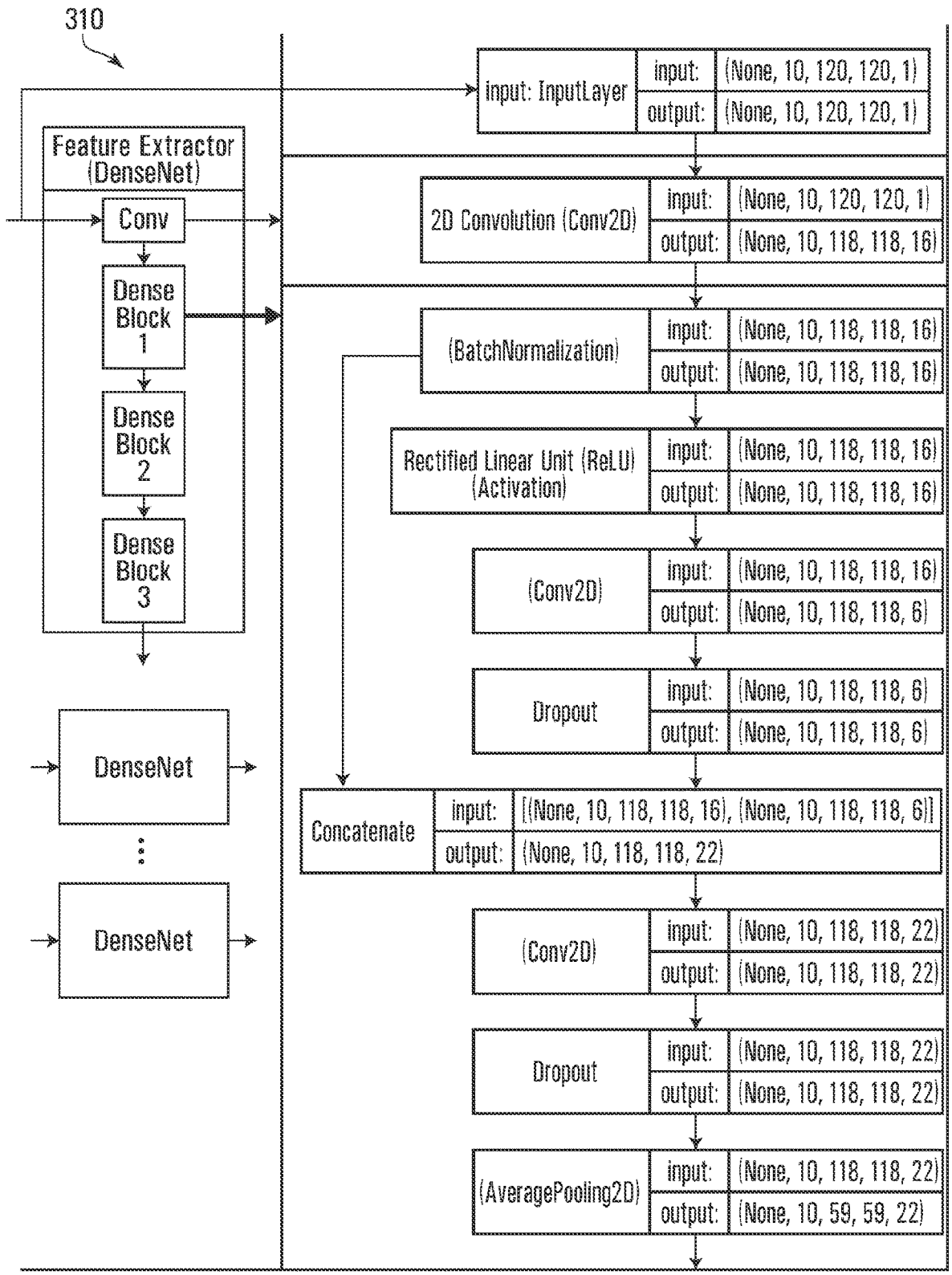
FIG. 6 is a representation of part of the neural network shown in FIG. 5 in accordance with various embodiments of the present disclosure.
Figure 7:
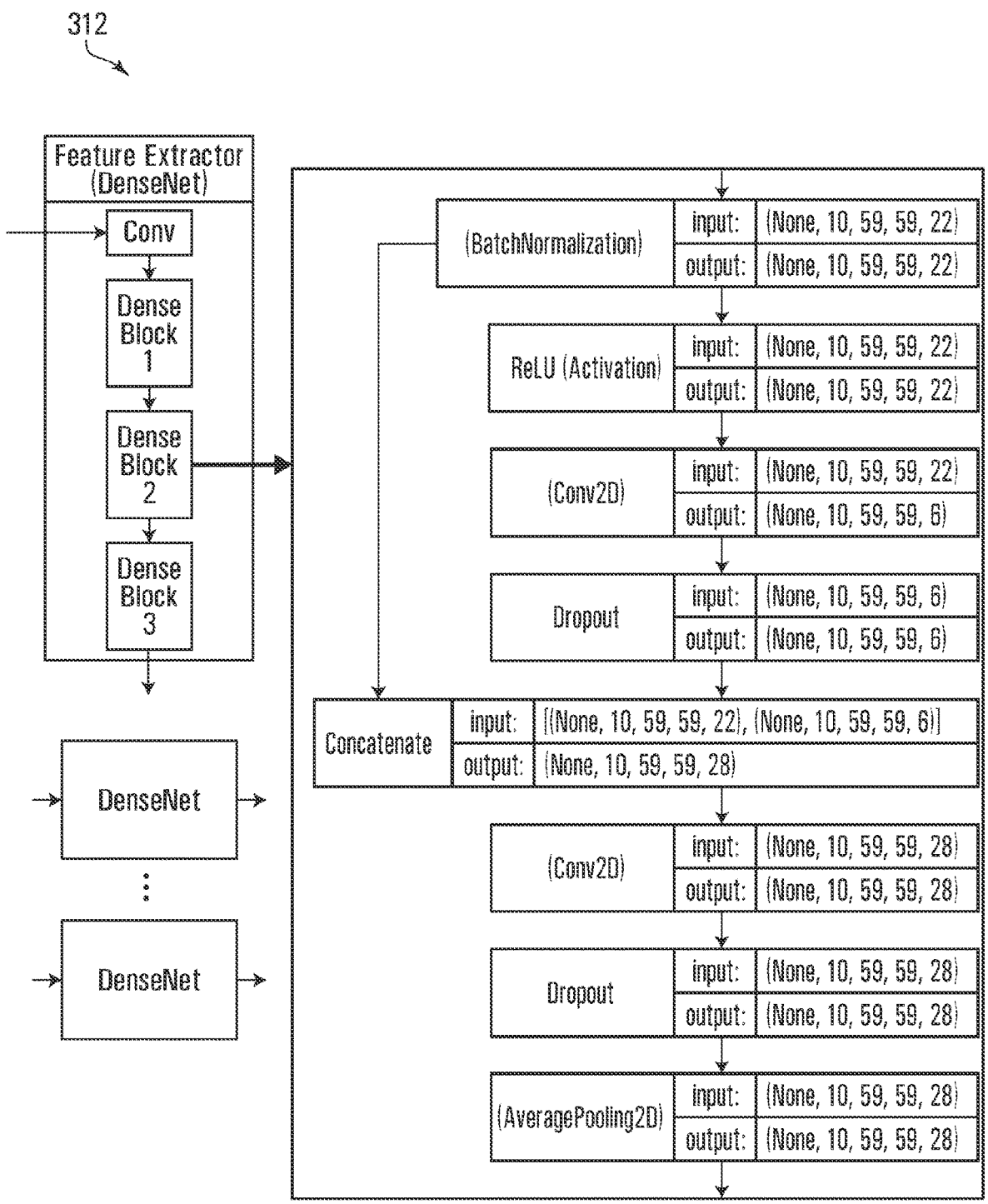
FIG. 7 is a representation of part of the neural network shown in FIG. 5 in accordance with various embodiments of the present disclosure.
Figure 8:
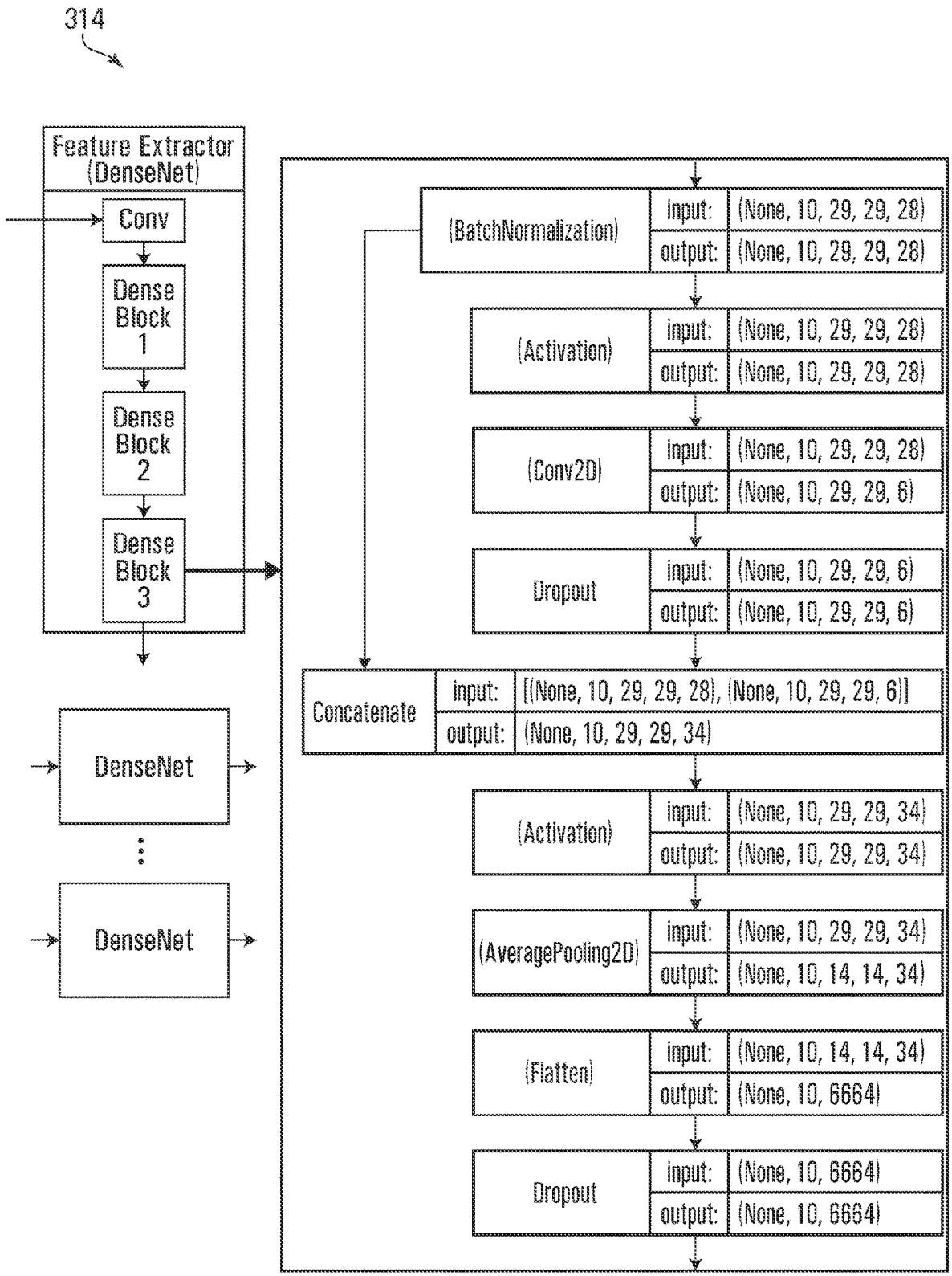
FIG. 8 is a representation of part of the neural network shown in FIG. 5 in accordance with various embodiments of the present disclosure.

An exemplary implementation of portions of the commonly defined first feature extracting neural networks including dense blocks 1, 2, and 3 in accordance with various embodiments is shown at 310, 312, and 314 in FIGS. 6, 7, and 8, respectively.

In some embodiments, the commonly defined first feature extracting neural networks (e.g., 304, 306, and 308 shown in FIG. 5) may be each configured to extract features that are encodings of image patterns of a single echo frame which are correlated with the image quality and view category of the single input echo frame. In some embodiments, these features (encodings or mappings) may be in the form of a vector of real-valued numbers (after the flatten operation), and each number may be considered as the level of presence of a specific spatial pattern in the input echo frame. In various embodiments, alternative or additional feature extracting functions and/or neural networks may be used to extract features of the input set of ultrasound images.

In some embodiments, more than one of the commonly defined first feature extracting neural networks may be run concurrently. For example, in some embodiments, block 204 may direct the analyzer processor 100 to run three of the commonly defined first feature extracting neural networks as three identical Convolutional Neural Networks (CNN-1, CNN-2, or CNN-3) in separate threads at the same time in order to prevent lag during particularly long inference times.

In various embodiments, the first feature representations (e.g., as shown at 320, 322, and 324 shown in FIG. 5) output by the commonly defined first feature extracting neural networks 304, 306, and 308 may act as first feature representations of the set of images received at block 202 of the flowchart. In some embodiments, for example, the first feature representations may each represent a tensor having dimensions 14×14×34 which is flattened to a tensor having length 6664 such that it can be input into a second feature extracting neural network 340.

Block 204 may direct the analyzer processor 100 to store the extracted first feature representations in the storage memory 104, for example, in a feature buffer which may be shared between all three threads. Once all of the images included in the set of images have been input to an instance of the commonly defined first feature extracting neural network, block 204 may direct the analyzer processor 100 to input the stored first feature representations into the second feature extracting neural network 340 shown in FIG. 5 to generate respective second feature representations, each associated with one of the ultrasound images.

Figure 5:
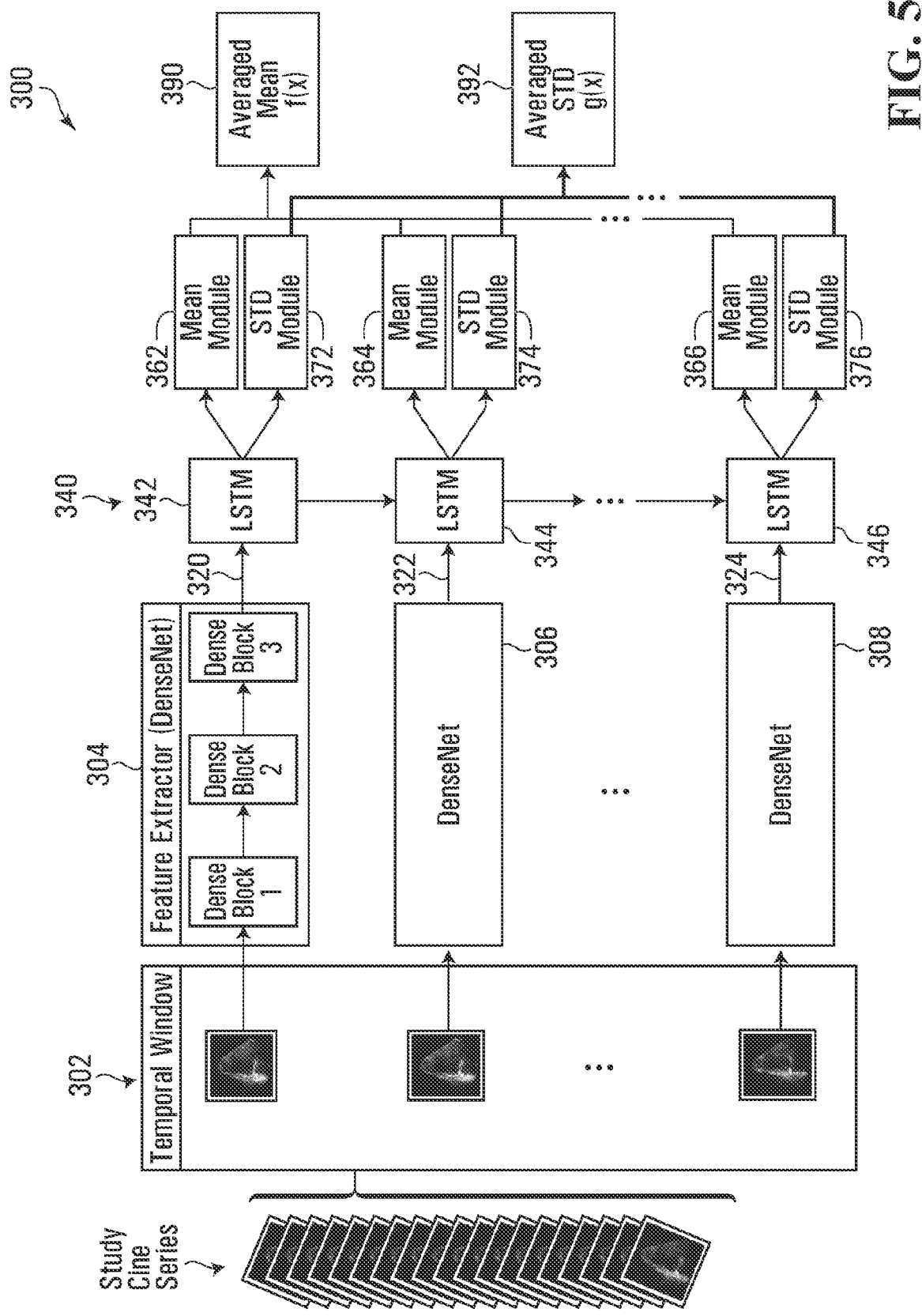
FIG. 5 is a representation of a quality assessment mean and standard deviation neural network function that may be used in the system shown in FIG. 2 in accordance with various embodiments of the present disclosure.

Referring to FIG. 5, in some embodiments, the second feature extracting neural network 340 may include a plurality of recurrent neural networks (RNNs) (e.g., 342, 344, and 346 shown in FIG. 4). In some embodiments, the RNNs may each be implemented using a long short term memory module (LSTM). In some embodiments, parameters defining the second feature extracting neural network 340 may be stored in the location 156 of the storage memory 104 and block 204 may direct the analyzer processor 100 to retrieve the parameters from the location 156 of the storage memory 104. Referring to FIG. 5, each RNN (e.g., 342, 344, and 346 shown in FIG. 5) may output a respective second feature representation, which may be used as an input for further processing. In various embodiments, each of the second feature representations may be a tensor having a length of 128.

In some embodiments, the LSTM layer (which is a type of RNN layer) may operate on the outputs of the DenseNet networks of multiple frames. As a result, in some embodiments, the features extracted by the LSTM networks may be encodings of both spatial and temporal patterns of a multitude of echo frames. The sequence of frames whose spatial and temporal patterns contribute to the extracted features may depend on the type of RNN layer included in the second feature extracting neural network 340. In some embodiments, conventional RNN architectures may look backward in time and extract features from the previous N (e.g., N=10) frames. However, in various embodiments, other types of RNNs may be considered/used (i.e. bidirectional RNN) where features may be extracted from the collective of previous and future frames. In various embodiments, the number of frames included in the feature extraction of the RNNs (such as LSTM) could be N=10 or more. In some embodiments, the features may be in the form of real-valued numbers (for example, the features may usually be between −1 and 1 as the activation function of RNN is usually hyperbolic tangent). In some embodiments, each number may be considered as representing a level of presence of a specific spatial and temporal pattern.

Referring to FIG. 4, in various embodiments, block 204 may direct the analyzer processor 100 to apply numerical quality assessment mean neural network functions or neural networks (e.g., 362, 364, and 366 as shown in FIG. 5) to the second feature representations to determine respective numerical quality assessment means from each of the second feature representations. In some embodiments, the numerical quality assessment mean neural network functions may include logistic regression modules.

In some embodiments, block 204 may direct the analyzer processor 100 to average the determined numerical quality assessment means to determine an average mean 390. In various embodiments, block 204 may direct the analyzer processor 100 to store the average mean in the location 144 of the storage memory 104 as a property distribution mean. For example, in some embodiments, the average mean may be determined to be about 0.675.

In various embodiments, block 204 may direct the analyzer processor 100 to apply numerical quality assessment standard deviation neural network functions (e.g., 372, 374, and 376 as shown in FIG. 5) to determine respective numerical quality assessment standard deviations or variance parameters from each of the second feature representations. In some embodiments, the numerical quality assessment standard deviation neural network functions may include logistic regression modules. In some embodiments, block 204 may direct the analyzer processor 100 to average the determined numerical quality assessment standard deviations to determine an average standard deviation 392. In various embodiments, block 204 may direct the analyzer processor 100 to store the average standard deviation in the location 146 of the storage memory 104 as a property distribution standard deviation. For example, in some embodiments, the average standard deviation may be determined to be about 0.075.

In some embodiments, the total number of parameters in the neural network function 300 may be about 3.5 million.

Referring back to FIG. 4, block 206 directs the analyzer processor 100 to cause a cumulative distribution function defined at least in part by the at least one property confidence distribution parameter to be applied to a plurality of ranges, each range associated with a respective property that may be associated with the set of images, to determine a plurality of property confidences, each of the property confidences representing a confidence that the set of images should be associated with a respective one of the properties.

For example, in some embodiments, the properties may be quality assessments of the ultrasound images received at block 202. The quality assessments may be "Poor" associated with a numerical quality assessment of (0–0.25], "Fair" associated with a numerical quality assessment of (0.25–0.5], "Good" associated with a numerical quality assessment of (0.5–0.75], and "Excellent" associated with a numerical quality assessment of (0.75–1.00]. In various embodiments, the properties or categories and associated ranges may have been previously provided and may have been used during training of the neural network. In some embodiments, the properties and ranges may be stored in the storage memory 104, such as in the location 142 of the storage memory 104. In some embodiments, the ranges at the high and low ends may be open ended. For example, in some embodiments, "Poor" may be associated with a numerical quality assessment of (−∞–0.25] and "Excellent" may be associated with a numerical quality assessment of (0.75 to +∞].

In various embodiments, block 206 may direct the analyzer processor 100 to use a Gaussian cumulative distribution function defined using the property distribution mean and the property distribution standard deviation stored in the locations 144 and 146 of the storage memory 104. For example, block 206 may direct the analyzer processor 100 to use the following Gaussian cumulative distribution function:

$$\hat{p}_c^* = F(u_c) - F(l_c)$$
$$= \frac{1}{2}\left(\mathrm{erf}\left(\frac{u_c - f(x)}{g(x)\sqrt{2}}\right) - \mathrm{erf}\left(\frac{l_c - f(x)}{g(x)\sqrt{2}}\right)\right)$$

where $u_c$ is the upper limit of the range, $l_c$ is the lower limit of the range, $f(x)$ is the average mean determined at block 204, and $g(x)$ is the average standard deviation determined at block 204, and where:

$$\mathrm{erf}(z) = \frac{2}{\sqrt{\pi}} \int_0^z \exp(-t^2) dt$$

In some embodiments, observations of samples with quality below "Poor" or above "Excellent" may be ignored and so block 206 may direct the analyzer processor 100 to normalize the determined confidences or probabilities to ensure a unit sum:

$$\hat{p}_c = \frac{\hat{p}_c^*}{\sum_{c \in C} \hat{p}_c^*}$$

Figure 9:
FIG. 9 is a representation of an exemplary property confidence record that may be used in the system shown in FIG. 2 in accordance with various embodiments of the present disclosure.

In some embodiments, using the above-noted ranges for quality assessments of "Poor", "Fair", "Good", and "Excellent" for a mean of 0.675 and a standard deviation of 0.075 may result in normalized confidences of 0, 0.01, 0.83, and 0.16, respectively. In various embodiments, block 206 may direct the analyzer processor 100 to store the determined confidences in the location 148 of the storage memory 104. For example, in some embodiments, block 206 may direct the analyzer processor 100 to store a property confidence record 500 as shown in FIG. 9 in the location 148 of the storage memory 104. In various embodiments, the property confidence record 500 may include property identifier fields 502, 506, 510, and 514, each associated with a confidence field 504, 508, 512, and 516 respectively. In various embodiments, block 206 may direct the analyzer processor 100 to store the determined normalized confidences in the confidence fields 504, 508, 512, and 516.

Figure 10:
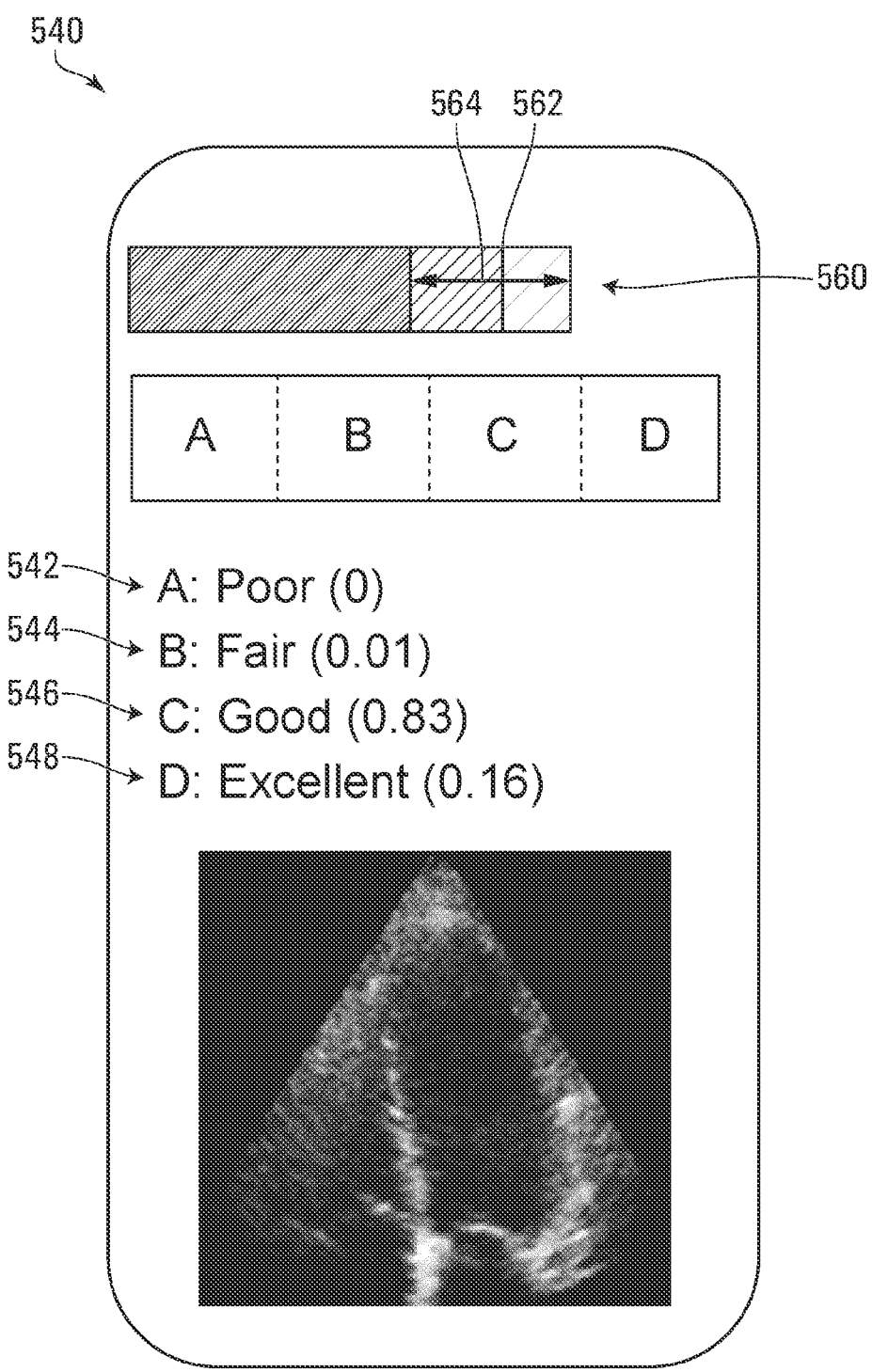
FIG. 10 is a representation of an exemplary display that may be displayed by the system shown in FIG. 2 in accordance with various embodiments of the present disclosure.

In some embodiments, the flowchart 200 may include blocks of code for directing the analyzer processor 100 to produce signals for causing the display 24 shown in FIG. 2 to display a representation of at least one of the property confidences. For example, in some embodiments, the blocks of code may include blocks for directing the analyzer processor 100 to produce signals for causing the display 24 to display a depiction 540 of the determined normalized confidences, as shown in FIG. 10. Referring to FIG. 10, in some embodiments, the normalized confidences may be displayed in text at 542, 544, 546, and 548 respectively.

In some embodiments, the flowchart 200 may include blocks of code for directing the analyzer processor 100 to produce signals for causing the display 24 to display a representation of the at least one property confidence distribution parameter. For example, in various embodiments, the depiction 540 may include representations of the average mean and/or the average standard deviation as determined in block 206. In some embodiments, the blocks of code may direct the analyzer processor 100 to cause the depiction 540 to include a multi-shaded bar 560 representing the property distribution mean and the property distribution standard deviation. For example, in the depiction 540 shown in FIG. 10, a position 562 of the multi-shaded bar 560 may coincide with the property distribution mean and a width 564 of the multi-shaded end portion of the bar 560 may represent the standard deviation.

In various embodiments, displaying to the user the property confidences and/or the mean and standard deviation, may allow the user to have a better understanding of the aleatoric uncertainty that may be present in the predicted properties. In some embodiments, for example, where a user is viewing confidences associated with quality assessments of echocardiographic views, understanding the magnitude of uncertainty associated with a quality assessment of a view, may allow the user to reconfigure the ultrasound machine and/or the transducer to try to improve the uncertainty and/or quality assessment.

Neural Network Training

Figure 11:
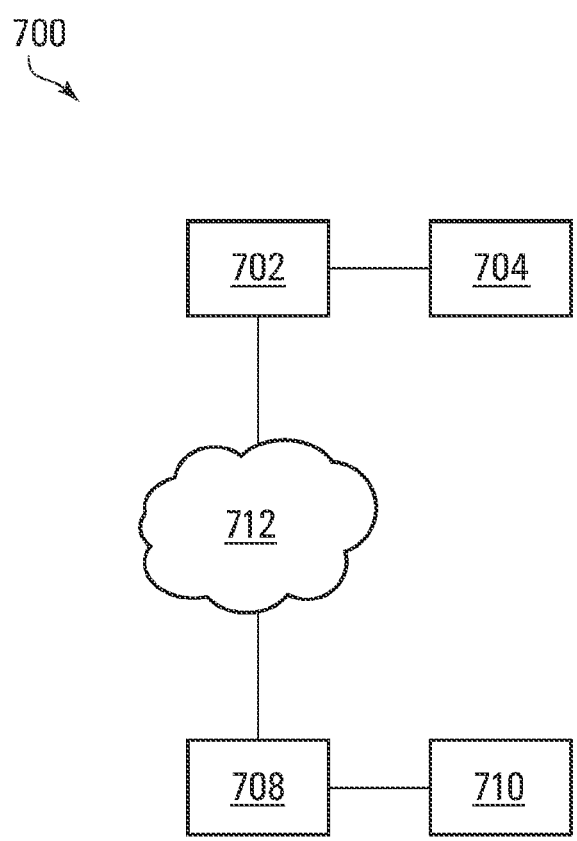
FIG. 11 is a schematic view of a system for facilitating image analysis including training at least one neural network function according to various embodiments of the present disclosure.

As discussed above, in various embodiments, parameters defining the quality assessment mean and standard deviation neural network function may be stored in the location 142 of the storage memory 104 of the image analyzer 12. In some embodiments, the parameters may have been generated during neural network training. Referring now to FIG. 11 there is shown a system 700 for facilitating image analysis including training at least one neural network function, in accordance with various embodiments.

Referring to FIG. 11, the system 700 includes an image analyzer 702 in communication with an image data source 704. In various embodiments, the image analyzer 702 and the image data source 704 may include functionality generally similar to that described herein having regard to the image analyzer 12 and the image data source 14 shown in FIGS. 1 and 2. In some embodiments, the image analyzer 702 may use as an input, ultrasound images and use a neural network to determine a quality assessment mean and standard deviation and to determine confidences for various quality assessments based on the quality assessment mean and standard deviation as applied to ranges.

Referring to FIG. 11, in various embodiments, the system 700 also includes a neural network trainer 708 in communication with a training data source 710. In various embodiments, the image analyzer 702 may be in communication with the neural network trainer 708 via a communication network 712, which may in some embodiments, include the Internet, and/or remote mass storage for example.

In operation, the neural network trainer 708 may be configured to use training image data taken from the training data source 710 to train at least one neural network function, such as, for example a quality assessment mean and standard deviation neural network function described herein with regard to the system 10 shown in FIG. 1, and to provide the parameters defining the at least one neural network function to the image analyzer 702 shown in FIG. 11.

Figure 12:
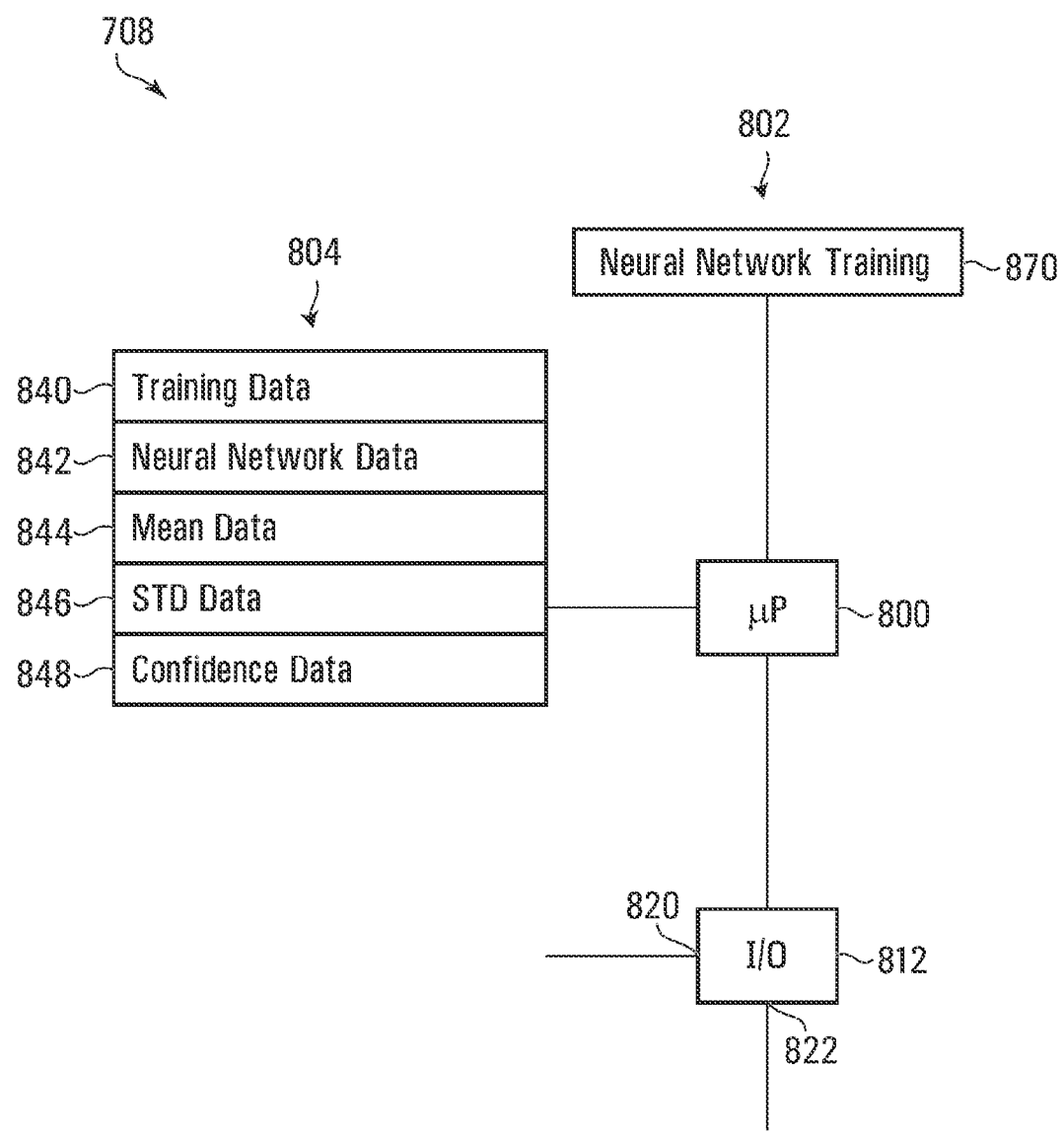
FIG. 12 is a schematic view of a neural network trainer of the system shown in FIG. 11 including a processor circuit in accordance with various embodiments of the present disclosure.

Referring to FIG. 12, a schematic view of the neural network trainer 708 of the system 700 shown in FIG. 11 according to various embodiments is shown. In various embodiments, elements of the neural network trainer 708 that are similar to elements of the image analyzer 12 shown in FIG. 3 may function generally as described herein having regard to the image analyzer 12 shown in FIG. 3. In various embodiments, the neural network trainer 708 may be implemented as a server, for example.

Referring to FIG. 12, the neural network trainer 708 includes a processor circuit including a trainer processor 800 and a program memory 802, a storage memory 804, and an input/output (I/O) interface 812, all of which are in communication with the trainer processor 800.

The I/O interface 812 includes an interface 820 for communicating with the training data source 710 shown in FIG. 11 and an interface 822 for communicating with the image analyzer 702 via the network 712.

Processor-executable program codes for directing the trainer processor 800 to carry out various functions are stored in the program memory 802. Referring to FIG. 11, the program memory 802 includes a block of codes 870 for directing the neural network trainer 708 to perform facilitating neural network training functions.

The storage memory 804 includes a plurality of storage locations including location 840 for storing training data, location 842 for storing neural network data, location 844 for storing mean data, location 846 for storing standard deviation data, and location 848 for storing confidence data.

In some embodiments, the program memory 802, the storage memory 804, and/or any portion thereof may be included in a device separate from the neural network trainer 708 and in communication with the neural network trainer 708 via the I/O interface 812, for example. In some embodiments, the functionality of the trainer processor 800 and/or the neural network trainer 708 as described herein may be implemented using a plurality of processors and/or a plurality of devices, which may be distinct devices which are in communication via respective interfaces and/or a network, such as the Internet, for example.

Figure 13:
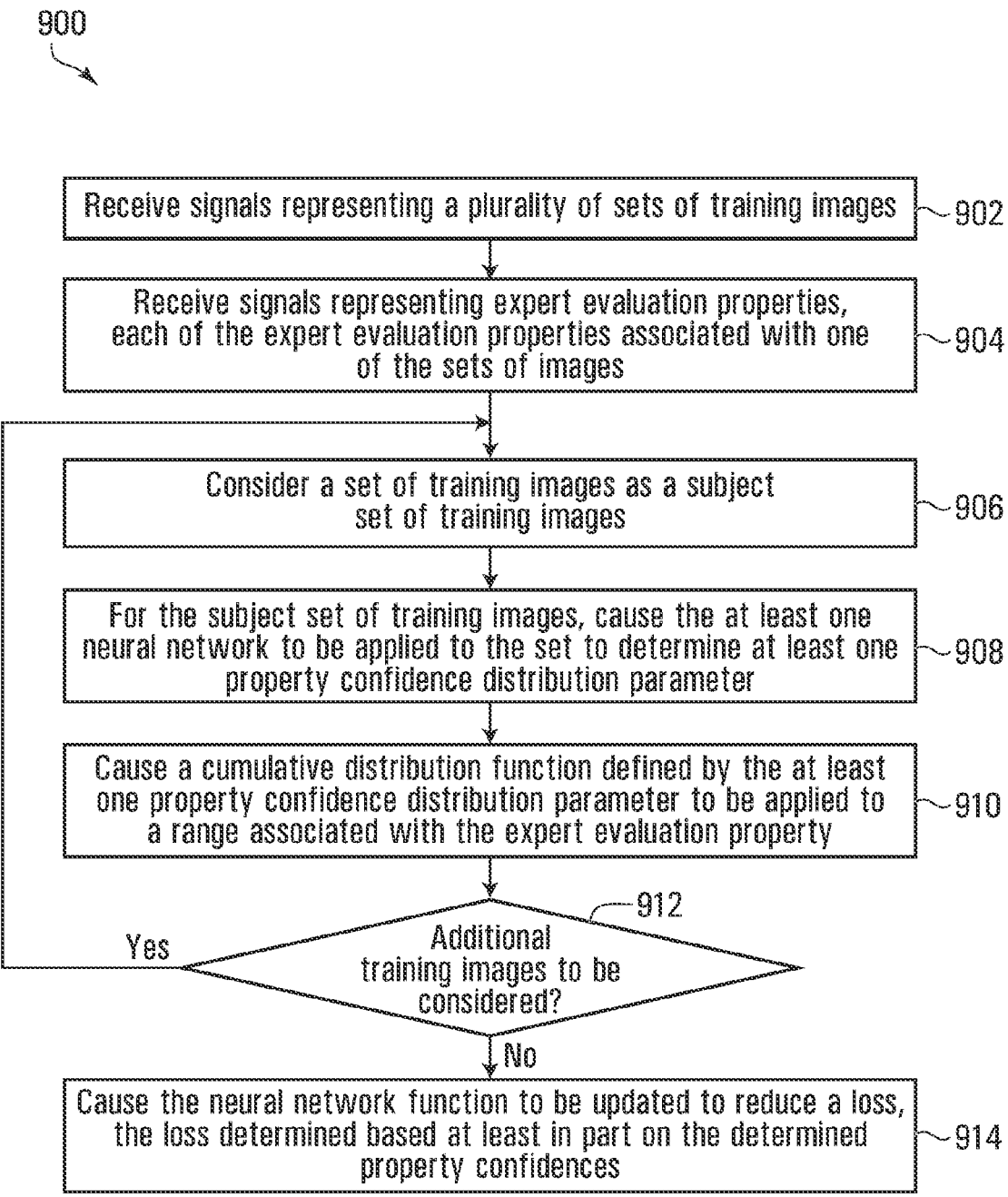
FIG. 13 is a flowchart depicting blocks of code for directing the neural network trainer of the system shown in FIG. 11 to perform facilitating neural network image analysis functions in accordance with various embodiments of the present disclosure.

In various embodiments, the neural network trainer 708 shown in FIGS. 11 and 12 may be configured to facilitate neural network training. Referring to FIG. 13, a flowchart depicting blocks of code for directing the trainer processor 800 shown in FIG. 12 to facilitate neural network training functions in accordance with various embodiments is shown generally at 900. The blocks of code included in the flowchart 900 may be encoded in the block of codes 870 of the program memory 802 shown in FIG. 12, for example.

Figure 14:
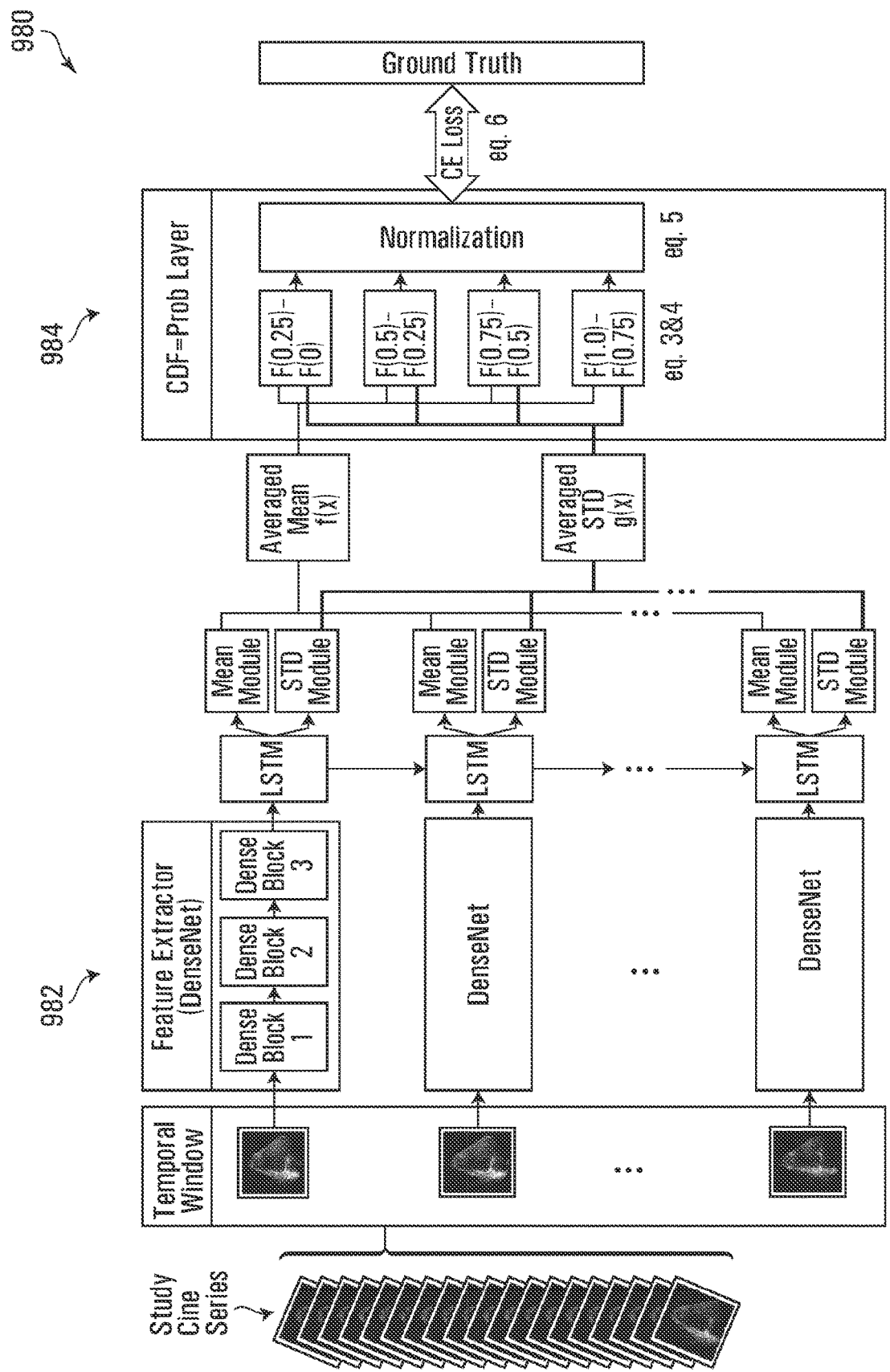
FIG. 14 is a representation of a neural network function that may be trained in the system shown in FIG. 11 in accordance with various embodiments of the present disclosure.

In various embodiments, the blocks included in the flowchart 900 may direct the trainer processor 800 to train a neural network function as depicted at 980 in FIG. 14, for example. In various embodiments, the neural network function 980 may include a quality assessment mean and standard deviation neural network function 982 having an architecture corresponding to the quality assessment mean and standard deviation neural network function 300 shown in FIG. 5, with a cumulative distribution function 984 applied using the mean and standard deviation outputs of the quality assessment mean and standard deviation neural network function 982, such that the neural network function 980 is configured to output quality assessment confidences, each associated with a respective quality assessment. In various embodiments, the blocks included in the flowchart 900 may direct the trainer processor 800 to train the neural network function 980, such as, by minimizing cross entropy loss calculated using the quality assessment confidences and quality assessments or labels provided by experts.

Referring to FIG. 13, the flowchart 900 begins with block 902 which directs the trainer processor 800 to receive signals representing a plurality of sets of training images. Block 904 then directs the trainer processor 800 to receive signals representing expert evaluation properties, each of the expert evaluation properties provided by an expert and associated with one of the sets of training images.

In some embodiments, for example, the training data source 710 may have previously been provided with training data including sets of training images and an associated quality assessment for each of set of training images. In some embodiments, for example, the training data source 710 may have stored thereon training data for a plurality of ultrasound sessions wherein the data includes for each ultrasound session, a plurality of training ultrasound images, which may be included in an echocine series, for example, and an associated quality assessment which may include a representation of "Poor", "Fair", "Good" or "Excellent" for example. In various embodiments, the quality assessments may act as expert evaluation properties and may have been provided by a medical professional based on the medical professional's expert assessment of the quality of the set of images.

Figure 15:
FIG. 15 is a representation of an exemplary ultrasound session training record that may be used in the system shown in FIG. 11 in accordance with various embodiments of the present disclosure.

Referring to FIG. 15, a representation of an exemplary ultrasound session training record that may be included in the training data is shown at 1000. The ultrasound session training record 1000 includes a session identifier field 1002 for storing a unique identifier identifying the session, and a plurality of image fields 1004 for storing training images representing a video or cine series, which may be a temporally ordered set of images. In some embodiments, the training images may represent an echocardiographic cine series, for example, showing a patient's heart over time.

Referring to FIG. 15, the ultrasound session training record 1000 also includes a quality assessment field 1006 for storing a representation of a quality assessment associated with the training images from the image fields 1004. In some embodiments, the value for the quality assessment field 1006 may have been previously provided by medical professionals, who may have reviewed the associated training images and assessed their quality.

Referring back to FIG. 13, in various embodiments, blocks 902 and 904 may be executed concurrently and may direct the trainer processor 800 to receive ultrasound training session records, each having format generally similar to the ultrasound session training record 1000 shown in FIG. 15, from the training data source 710 via the interface 820 of the I/O interface 812 shown in FIG. 12, for example. In some embodiments, blocks 902 and 904 may direct the trainer processor 800 to store representations of the ultrasound training session records in the location 840 of the storage memory 804 shown in FIG. 12.

In view of the foregoing, after execution of blocks 902 and 904, the neural network trainer 708 may have stored in the location 840 of the storage memory 804 sets of images and a respective quality assessment associated with each of the sets of images. In various embodiments, this information may act as training data which may be used to train the quality assessment mean and standard deviation neural network function 980 shown in FIG. 14, as described below.

In some embodiments, the training data may be denoted as D={X, A}, where $X=\{x_i\}_{i=1}^{|D|}$ denote the sets of |D| observed samples (i.e., the sets of training images) and $A=\{a_i\}_{i=1}^{|D|}$ denote the corresponding quality assessments. In some embodiments, the neural network may be defined by W=the set of parameters or weights that define the quality assessment mean and standard deviation neural network function 982 shown in FIG. 14. In some embodiments, blocks 906 to 912 of the flowchart 900 shown in FIG. 13 may be configured to train or update the parameters defining the quality assessment mean and standard deviation neural network function such that likelihood over A is maximized, for example, by minimizing a loss function defined as:

$$l(W, D) = -\frac{1}{|D|}\sum_{i=1}^{D}(\log p(a_i | x_i, W))$$

where $p(a_i|x_i,W)$ denotes the confidence or probability associated with the quality assessment $a_i$ (from the training data) when the associated set of images $x_i$ are input into the quality assessment mean and standard deviation neural network function 982 defined by the parameters W. In some embodiments, $p(a_i|x_i,W)$ may be determined by inputting the set of images $x_i$ into the quality assessment mean and standard deviation neural network function 982 to determine a mean and standard deviation, and using a cumulative distribution function defined by the determined mean and standard deviation to determine $p(a_i|x_i,W)$ to be the confidence associated with the quality assessment identified by $a_i$.

Referring to FIG. 13, in various embodiments, blocks 906 to 912 may be executed to train or update the parameters defining the quality assessment mean and standard deviation neural network function 982 to minimize or reduce the loss function defined above.

Block 906 directs the trainer processor 800 to consider a set of the training images as a subject set of training images. In some embodiments, upon a first execution of block 906, block 906 may direct the trainer processor 800 to consider a first set of training images from one of the ultrasound session training records stored in the location 148 of the storage memory 104 (e.g., the ultrasound session training record 1000 shown in FIG. 15). For example, in some embodiments, block 906 may direct the trainer processor 800 to consider 10 of the training images from the ultrasound session training record 1000 shown in FIG. 15 as a subject set of training images.

Blocks 908 and 910 may then be executed for the subject set of training images. In various embodiments, blocks 908 and 910 may include code for functionality generally similar to blocks 204 and 206 of the flowchart 200 shown in FIG. 4. Block 908 directs the trainer processor 800 to, for the subject set of training images, cause the at least one neural network function to be applied to the set of training images to determine at least one property confidence distribution parameter. For example, in some embodiments, block 908 may direct the trainer processor 800 to cause the quality assessment mean and standard deviation neural network function 982 to be applied to the subject set of training images to determine a mean and standard deviation for the set of training images. In some embodiments, block 908 may direct the trainer processor 800 to store the determined mean and standard deviation in the locations 844 and 846 of the storage memory 804, for example.

Block 910 then directs the trainer processor 800 to cause a cumulative distribution function defined at least in part by the at least one property confidence distribution parameter to be applied to a range associated with the expert evaluation property associated with the set of images, to determine a property confidence representing a confidence that the set of images should be associated with the expert evaluation property. For example, where the quality assessment field 1006 associated with the subject set of images stores a representation of "Good", block 910 may direct the trainer processor 800 to use a range of (0.5–0.75] and the Gaussian cumulative distribution function, described herein in connection with block 206 of the flowchart 200 shown in FIG. 4, to determine the property confidence.

In various embodiments, block 910 may direct the trainer processor 800 to store the determined confidence in the location 848 of the storage memory 804. In some embodiments, block 910 may direct the trainer processor 800 to store the determined confidence in association with the set of training images from which it was determined. For example, in some embodiments, block 910 may direct the trainer processor to store a training confidence record 1020 as shown in FIG. 16 in the location 848 of the storage memory 804. Referring to FIG. 16, the training confidence record 1020 includes a session identifier field 1022 for associating the confidence with a session and a confidence field 1024 for storing the determined confidence.

In various embodiments, after execution of block 910, block 912 may direct the trainer processor 800 to determine whether there are any additional training images to be considered. For example, in some embodiments, block 912 may direct the trainer processor 800 to determine whether all of the sets of training images received at block 902 have been considered. If at block 912, it is determined that additional training images are to be considered, the trainer processor 800 is directed to return to block 906 and consider another set of training images as the subject set of training images. Blocks 908 and 910 are then executed with the new subject set of training images.

If at block 912 it is determined that no further training images are to be considered, block 912 directs the trainer processor to proceed to block 914. In various embodiments, when the trainer processor 800 proceeds to block 914, there may be stored in the location 848 of the storage memory 804 numerous confidence records having format generally similar to the confidence record 1020 shown in FIG. 16.

Block 914 then directs the trainer processor to cause the at least one neural network function to be updated to reduce a loss, the loss determined based at least in part on the determined property confidences. In various embodiments, block 914 may direct the trainer processor to reduce the loss defined as follows:

$$l(W, D) = -\frac{1}{|D|}\sum_{i=1}^{D}(\log p(a_i | x_i, W))$$

by updating the parameters of the neural network function 982 as stored in the location 842 of the storage memory 804, where $p(a_i|x_i,W)$ has been determined as described above and is stored as the property confidences (for example, as stored in the confidence field 1024 of the confidence record 1020 shown in FIG. 16), for each of the sets of input images $x_i$.

In some embodiments, after block 914 has been completed, the trainer processor 800 may return to block 906 and the neural network may be further trained. In various embodiments, blocks 906-914 may be repeated numerous times to train the neural network function and try to minimize the loss function.

In various embodiments, the loss function may be reduced or minimized using an Adam optimizer to train the network end-to-end from scratch, for example. For example, in some embodiments, repeated execution of blocks 906-914 may be performed by using the Adam optimizer with the loss function as described above and thus incorporating the cumulative distribution function. In some embodiments, for the Adam optimizer, the initial learning rate may be set to 2.5e-4, decaying by scale 0.91 every two epochs, till it decays to approximately 100 times smaller at the 100th epoch. In some embodiments, the training image data may be augmented by using random translation up to 10% of image dimensions in pixels and random rotation up to ±5 degrees. In some embodiments, weight decay may be set to 5e-4.

In various embodiments, alternative or additional neural network training processes may be used. For example, in some embodiments, the neural network function 980 may be trained using stochastic gradient descent method (SGD), RMSprop, or another neural network training process.

In various embodiments, after blocks 906-914 have been executed one or more times, data defining a trained quality assessment mean and standard deviation neural network function may be stored in the location 842 of the storage memory 804.

In some embodiments, the flowchart 900 may include a block for directing the trainer processor 800 to produce signals representing the trained quality assessment mean and standard deviation neural network function 982 shown in FIG. 14 for causing a representation of the trained quality assessment mean and standard deviation neural network function 982 to be transmitted to the image analyzer 702 shown in FIG. 11. In some embodiments, the image analyzer 702 may include a processor circuit generally as shown in FIG. 3 and the image analyzer 702 may direct the analyzer processor of the image analyzer 702 to store the representation of the trained quality assessment mean and standard deviation neural network function in a location similar to the location 142 of the image analyzer 12 shown in FIG. 3.

In various embodiments, the image analyzer 702 may be configured to execute the flowchart 200 shown in FIG. 4, generally as described herein, to use the trained quality assessment mean and standard deviation neural network function and determine confidences associated with respective quality assessments, generally as described herein.

In some embodiments, a system for training may include simply the neural network trainer 708 and may omit the training data source 710, the network 712, the image analyzer 702, and/or the image data source 704.

Ejection Fraction

In some embodiments, an image analyzer that includes functionality generally similar to the image analyzer 12 shown in FIGS. 1-3 and described herein may be configured to facilitate neural network image analysis for alternative or additional types of properties, such as, for example, clinically relevant measurements, that may be associable with sets of images.

In some embodiments, for example, an image analyzer that includes functionality generally similar to the image analyzer 12 shown in FIGS. 1-3 may be configured to facilitate neural network image analysis relating to properties and/or characteristics of any or all of the following:

Aorta
Aortic prosthesis
Aortic Regurgitation
AV function
AV stenosis severity
AV structure
BAV
Filling
Filling pressure
Hypertrophy
LVEF
MAC
Mitral prosthesis
Mitral Regurgitation
MV function
MV stenosis severity
MV structure
Pericardial effusion
Pulmonary regurgitation
Rhythm
RV function
RV structure
Tricuspid prosthesis
Tricuspid Regurgitation
TV function
TV structure
Wall motion An important clinical measurement of an echo exam may be left ventricular (LV) ejection fraction (EF), which evaluates the systolic performance of the heart, that is, the strength of contractile function. In some embodiments, LV EF may be estimated in clinics using systems that are configured to facilitate visual assessment of echo cine series and labeling or categorizing the LV EF based on the visual assessment. These systems may be used by experienced echocardiographers, who after years of practice, can subjectively estimate EF accurately. Visual assessment using such systems may be robust to segmentation and frame selection errors. However, visual assessment of LV EF using these systems may suffer from high inter and intra-observer variability, making EF estimation challenging. Factors contributing to such variability may include (1) low inherent image quality in echo; (2) inaccurate segmentation or key frame detection; and/or (3) errors due to volume estimation from 2D images.

Figure 17:
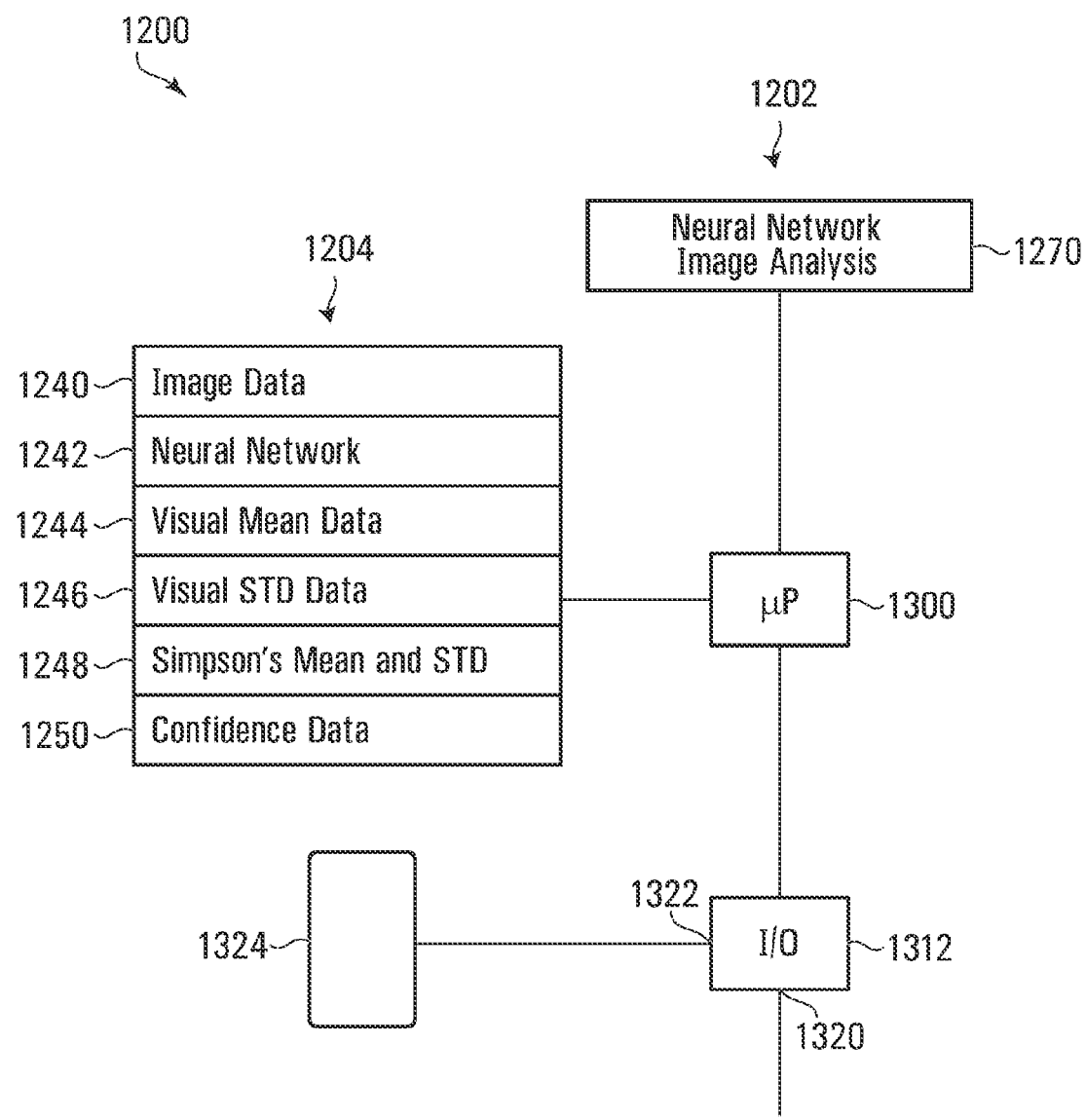
FIG. 17 is a schematic view of an image analyzer of a system for facilitating neural network image analysis functions in accordance with various embodiments of the present disclosure.

In some embodiments an image analyzer 1200 as shown in FIG. 17 may be configured to facilitate image analysis for determining LV EF or an estimated ejection fraction function diagnosis, based on at least visual assessment training data. The image analyzer 1200 may be included in a system having an architecture generally similar to the system 10 shown in FIG. 1 or 2 and the image analyzer 1200 may be in communication with an image data source. In various embodiments, the image analyzer 1200 may include some generally similar elements to the image analyzer 12 shown in FIG. 3. In various embodiments, the image analyzer 1200 may be configured to determine confidences associated with visual assessments of LV EF based on echocardiograms by applying a neural network and a cumulative distribution function.

In some embodiments, for example, the image analyzer 1200 may include functionality generally similar to the image analyzer 12 shown in FIG. 3, except that the image analyzer 1200 may be configured to determine confidences associated with different visual assessments of LV EF or estimated ejection fraction function diagnoses, such as "Severe dysfunction", "Moderate dysfunction", "Mild dysfunction", or "Normal function", which may be associated with ranges of [0.0–0.20], (0.20–0.40], (0.40–0.55], and (0.55–0.80), respectively, for example. Referring to FIG. 17, the image analyzer 1200 includes an analyzer processor 1300 in communication with a program memory 1202, storage memory 1204, and I/O interface 1312. The I/O interface includes an interface 1322 for communicating with a display 1324 and an interface 1320 for communicating with an image data source.

Figure 18:
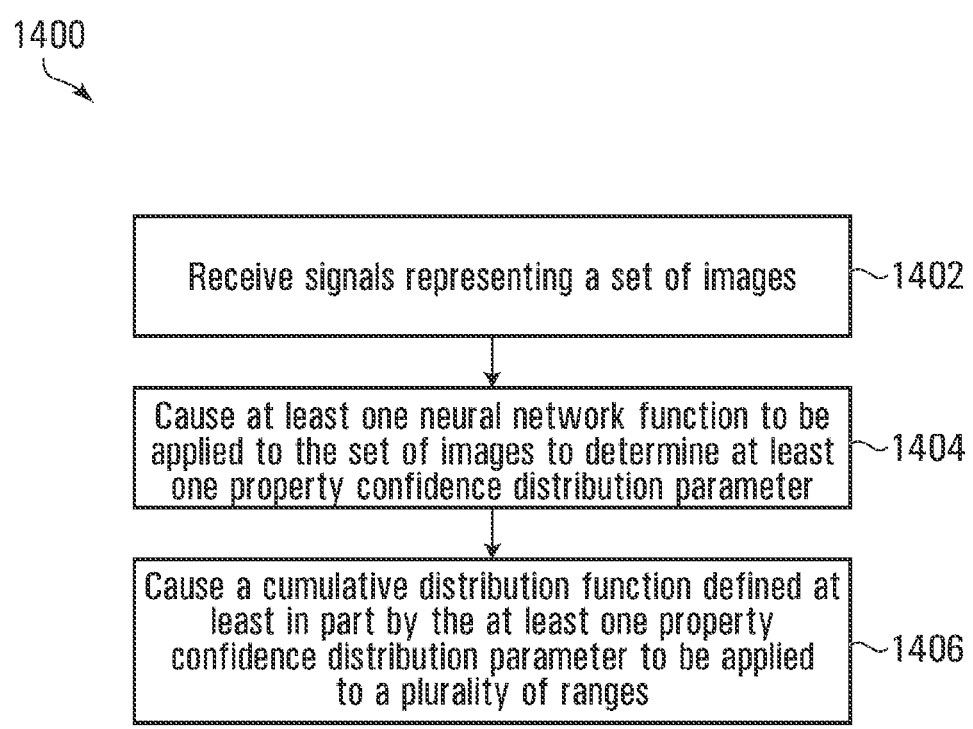
FIG. 18 is a flowchart depicting blocks of code for directing the image analyzer shown in FIG. 17 to perform facilitating neural network image analysis functions in accordance with various embodiments of the present disclosure.

Referring to FIG. 18, a flowchart depicting blocks of code for directing the analyzer processor 1300 shown in FIG. 17 to perform facilitating neural network image analysis functions in accordance with various embodiments is shown generally at 1400. The blocks of code included in the flowchart 1400 may be encoded in a block of codes 1270 of the program memory 1202 shown in FIG. 17, for example.

Referring to FIG. 18, block 1402 directs the analyzer processor 1300 to receive signals representing a set of images. In some embodiments, block 1402 may direct the analyzer processor 1300 to receive a set of ultrasound images including a set of A2C ultrasound images and a set of A4C ultrasound images. For example, in some embodiments, the set of images may be received from an image data source in communication with the image analyzer 1200. In some embodiments, block 1402 may direct the analyzer processor 1300 to store the received set of images in the location 1240 of the storage memory 1204 of the image analyzer 1200.

Figure 19:
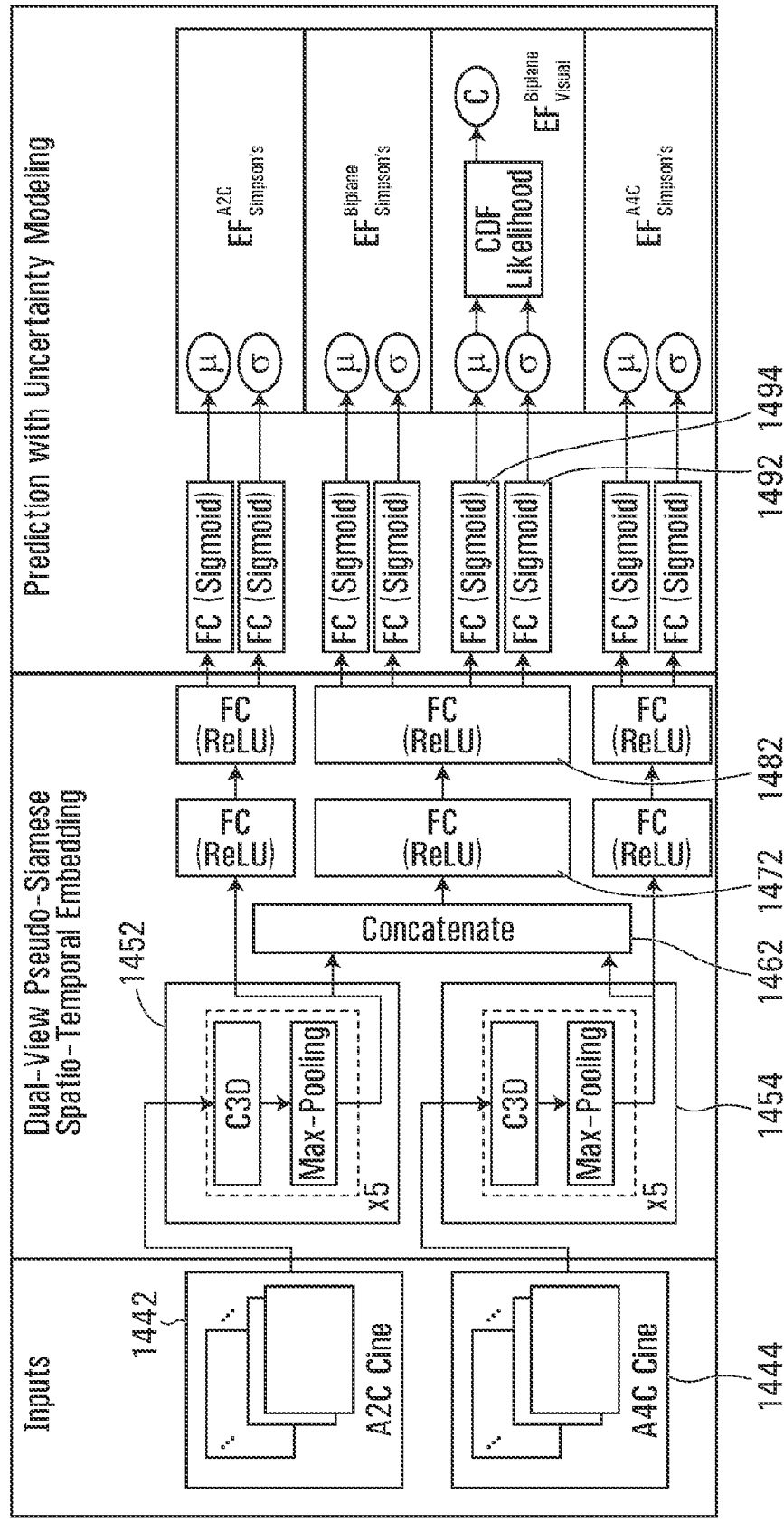
FIG. 19 is a representation of a LV EF assessment mean and standard deviation neural network function that may be used by the image analyzer shown in FIG. 17 in accordance with various embodiments of the present disclosure.

Block 1404 directs the analyzer processor 1300 to cause at least one neural network function to be applied to the set of images to determine at least one property confidence distribution parameter. In some embodiments, block 1404 may direct the analyzer processor 1300 to cause an LV EF assessment mean and standard deviation neural network function 1440 as shown in FIG. 19 to be applied to the set of images. In some embodiments, parameters defining the LV EF assessment mean and standard deviation neural network function 1440 may be stored in the location 1242 of the storage memory 1204 shown in FIG. 17, and block 1404 may direct the analyzer processor 1300 to retrieve the parameters and apply the neural network function 1440.

Referring to FIG. 19, the neural network function 1440 includes inputs 1442 and 1444 at which are input the sets of A2C and A4C ultrasound images, which may represent echo cine series from the A2C and A4C views, for example. 3D convolution (C3D) modules are then applied to the inputs in spatio-temporal feature embedding (STFE) blocks 1452 and 1454. C3D-based structures have proven promising for video analysis tasks, and despite being computationally expensive, are feasible for analyzing relatively short echo cine series, which capture a few heart beats. In various embodiments, the input sets of ultrasound images or video are represented as stacks of 2D video frames, creating a 3D tensor, consisting of two spatial and one temporal dimensions; H×W×F. The STFE blocks each contain five (3, 3, 3) C3D and (2, 2, 2) max-pooling layers.

The spatio-temporal feature vectors may be merged after the STFE blocks 1452 and 1454 through a concatenation layer 1462 and then the merged vector may be processed by first and second ReLU blocks 1472 and 1482. The result may then be passed through a mean determining sigmoid block 1492 configured to determine a numerical mean for the LV EF assessment and also passed through a standard deviation determining sigmoid block 1494 configured to determine a numerical standard deviation for the LV EF assessment.

In various embodiments, block 1404 may direct the analyzer processor 1300 to store the resulting mean and standard deviation from blocks 1492 and 1494 in the locations 1244 and 1246 of the storage memory 1204 shown in FIG. 17, for example.

In 2D echo, EF may also be calculated or estimated through Simpson's method by approximating the left ventricular volume from 2D area, once it is traced. Simpson's method may be done, for example, using a single plane or using biplane Simpson's method of disks. The biplane Simpson's method involves measuring the minimum, i.e., end-systolic (ESV), and maximum, i.e., end-diastolic (EDV), volumes of the LV by estimating the LV surface area in two standard 2D echo views, referred to as apical two-chamber (A2C) and apical four-chamber (A4C). Single plane Simpson's method may be applied on A2C or A4C imaging planes. The biplane method may result in a more fine-tuned/precise EF that is acquired once the two measurements (A2C Simpson's and A4C Simpson's) are merged. The accuracy of Simpson's method may be highly dependent on accurate (a) selection of end-diastolic (ED) and end-systolic (ES) frames; and/or (b) segmentation of the LV endocardium, in both apical windows.

Whereas the result of visual assessment of LV EF is a category, the result of the Simpson's method is a percentage or numerical value between 0 and 1.

In some embodiments, the neural network function 1440 may be configured to also determine numerical mean and standard deviations for each of the methods, $EF_{Simpson's}^{A2C}$, $EF_{Simpson's}^{A4C}$, and $EF_{Simpson's}^{Biplane}$. In various embodiments, the neural network function 1440 may include two streams, designated for A2C and A4C cine series. A pseudo-siamese structure may be utilized, in that, the streams have a similar architecture, but the parameters are not coupled. $EF_{Simpson's}^{A2C}$ and $EF_{Simpson's}^{A4C}$ are linked to the input A2C and A4C ultrasound images, respectively. The other two outputs $EF_{Visual}^{Biplane}$ and $EF_{Simpson's}^{Biplane}$ are linked to both A2C and A4C views as they involve biplane measurements. The model may have been previously trained by jointly minimizing losses for the four types of EF measurement.

Block 1404 may direct the analyzer processor 1300 to store representations of the determined mean and standard deviation values for $EF_{Simpson's}^{A2C}$, $EF_{Simpson's}^{A4C}$, and $EF_{Simpson's}^{Biplane}$ in the location 1248 of the storage memory 1204.

Block 1406 then directs the analyzer processor 1300 to cause a cumulative distribution function defined at least in part by the at least one property confidence distribution parameter to be applied to a plurality of ranges, each range associated with a respective property that may be associated with the set of images, to determine a plurality of property confidences, each of the property confidences representing a confidence that the set of images should be associated with a respective one of the properties.

In various embodiments, block 1406 may be generally similar to block 206 of the flowchart 200 shown in FIG. 4, except that the properties may be "Severe dysfunction", "Moderate dysfunction", "Mild dysfunction", and "Normal function", and the associated ranges may be [0.0-0.20], (0.20–0.40], (0.40–0.55], and (0.55–0.80) respectively.

Block 1406 may direct the analyzer processor 1300 to store a property confidence record 1540 as shown in FIG. 20 in the location 1250 of the storage memory 104. In various embodiments, the property confidence record 1540 may include property identifier fields 1542, 1546, 1550, and 1554, each associated with a confidence field 1544, 1548, 1552, and 1556 respectively.

In some embodiments, the flowchart 1400 may include blocks of code for directing the analyzer processor 1300 to produce signals for causing the display 1324 shown in FIG. 17 to display a representation of at least one of the property confidences. For example, the block may direct the analyzer processor 1300 to cause the display 1324 to display a representation of the information included in the property confidence record 1540 generally as described herein having regard to the quality assessment information.

Figure 21:
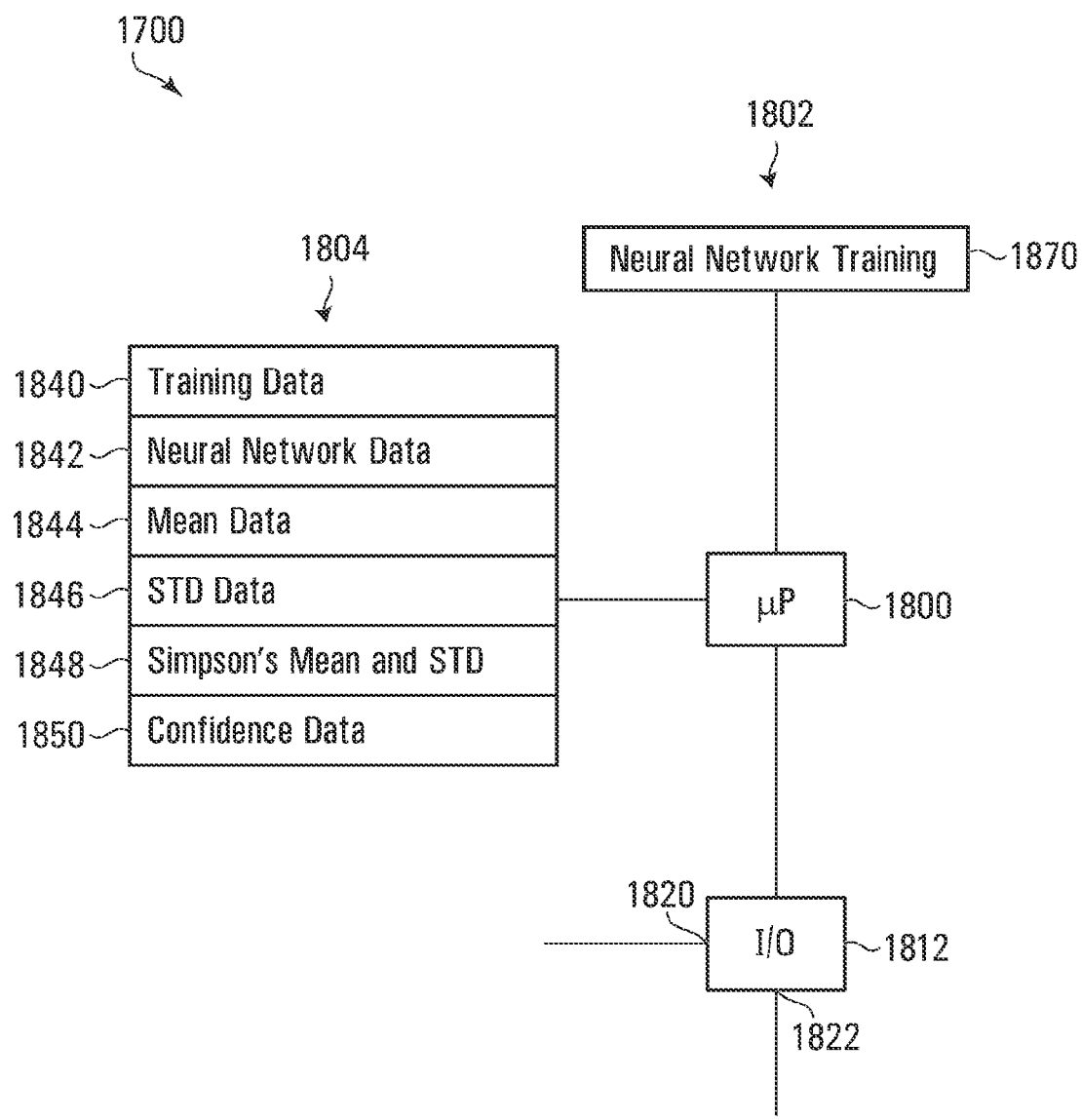
FIG. 21 is a schematic view of a neural network trainer of a system for facilitating image analysis including training at least one neural network function in accordance with various embodiments of the present disclosure.

Referring to FIG. 21, there is shown a neural network trainer 1700 configured to train the neural network function 1440 shown in FIG. 19, in accordance with various embodiments. In some embodiments, the neural network trainer 1700 may include functionality generally similar to the neural network trainer 708 shown in FIG. 12 and discussed herein. Referring to FIG. 21, the neural network trainer 1700 includes a trainer processor 1800 in communication with a program memory 1802, a storage memory 1804, and an I/O interface 1812. The I/O interface 1812 includes an interface 1820 for communicating with a training data source and an interface 1822 for communicating with an image analyzer.

In some embodiments, the neural network trainer 1700 may be included in a system having an architecture generally similar to the system 700 shown in FIG. 11. In various embodiments, the neural network trainer 1700 may be in communication with a training data source and an image analyzer generally similar to the image analyzer 1200 shown in FIG. 17.

Figure 22:
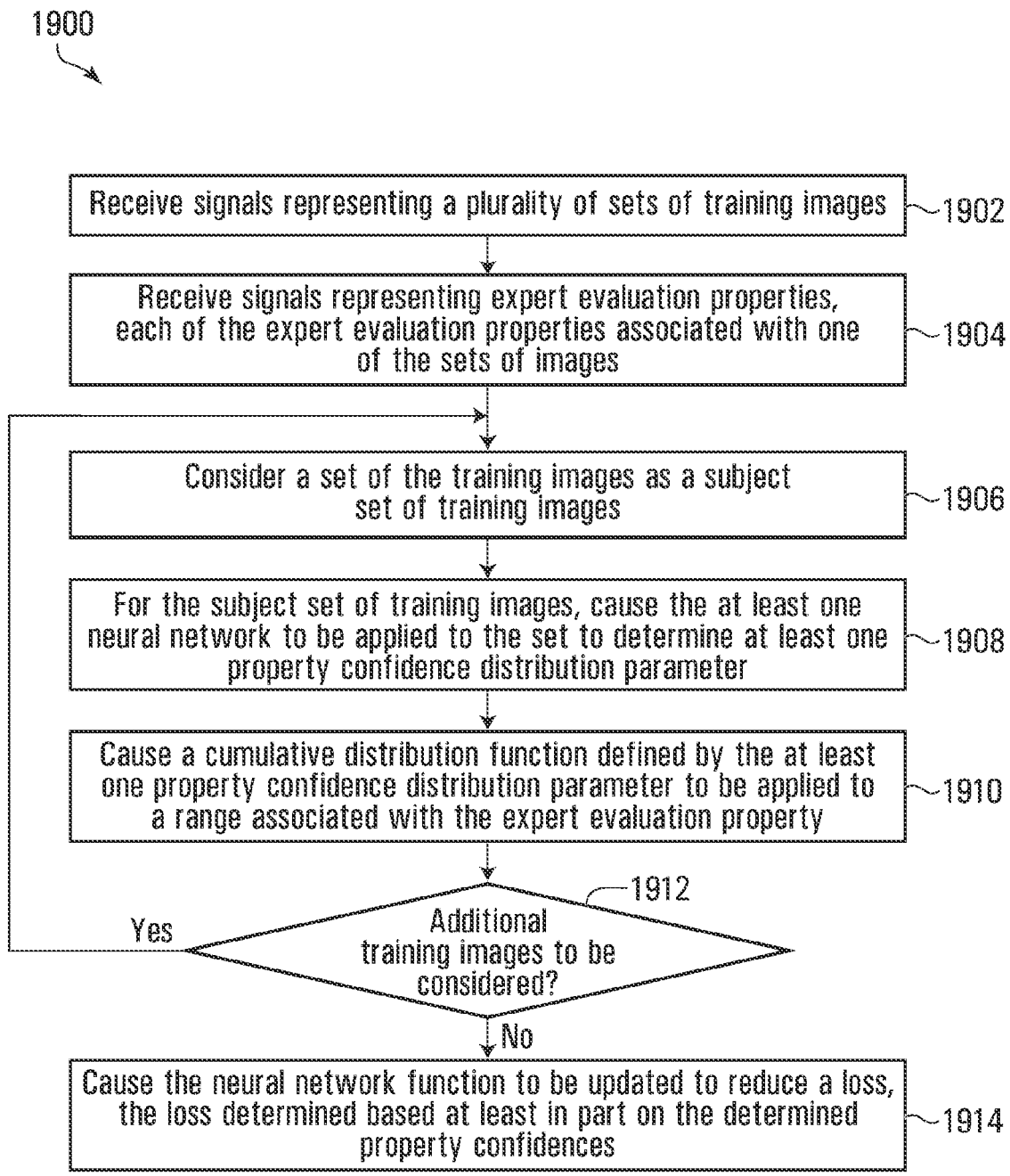
FIG. 22 is a flowchart depicting blocks of code for directing the neural network trainer shown in FIG. 21 to perform facilitating neural network training functions in accordance with various embodiments of the present disclosure.

Referring to FIG. 22, a flowchart depicting blocks of code for directing the trainer processor 1800 in FIG. 21 to perform facilitating neural network training functions in accordance with various embodiments is shown generally at 1900. The blocks of code included in the flowchart 1900 may be encoded in the block of codes 1870 of the program memory 1802 shown in FIG. 21, for example.

Referring to FIG. 22, the flowchart 1900 begins with block 1902 which directs the trainer processor 1800 to receive signals representing a plurality of sets of training images. Block 1904 directs the trainer processor 1800 to receive signals representing expert evaluation properties, each of the expert evaluation properties provided by an expert and associated with one of the sets of training images. In some embodiments, blocks 1902 and 1904 may be executed concurrently.

In some embodiments, for example, the training data source in communication with the neural network trainer 1700 may have previously been provided with training image data including sets of training images (including A2C and A4C views) and an associated visual assessment of LV EF for each of set of training images. In some embodiments, for example, the training data source may have stored thereon training data for a plurality of ultrasound sessions wherein the data includes for each ultrasound session, A2C training ultrasound images and A4C ultrasound images, which may be included in respective echocine series, for example, and an associated visual assessment of LV EF which may include a representation of "Severe dysfunction", "Moderate dysfunction", "Mild dysfunction", and "Normal function", for example. In various embodiments, the visual assessments of LV EF may act as expert evaluation properties and may have been provided by a medical professional based on the medical professional's expert visual assessment of the LV EF for the set of images.

In some embodiments, the training data may also include A2C, A4C and biplane Simpson's method assessments of the LV EF.

Referring to FIG. 24, a representation of an exemplary LV EF training record that may be included in the training data is shown at 2000. The LV EF training record 2000 includes a session identifier field 2002 for storing a unique identifier identifying the session, A2C image fields 2004 and A4C image fields 2006. The LV EF training record 2000 also includes a visual assessment of LV EF field 2008 for storing a representation of a visual assessment of LV EF which may have been previously provided by a medical professional when viewing the images stored in the image fields 2004 and 2006.

In some embodiments, the LV EF training record 2000 may also include an A2C Simpson's assessment of LV EF field 2010, an A4C Simpson's assessment of LV EF field 2012, and/or a Biplane Simpson's assessment of LV EF field 2014 for storing respective assessments provided by medical professionals using the respective methods.

Figure 23:
FIG. 23 is a representation of an exemplary LV EF training record that may be used by the neural network trainer shown in FIG. 21 in accordance with various embodiments of the present disclosure.

Referring back to FIG. 22, in various embodiments, blocks 1902 and 1904 may be executed concurrently and may direct the trainer processor 1800 to receive a plurality of LV EF training records, each having format generally similar to the LV EF training record 2000 shown in FIG. 23, from the training data source via the interface 1820 of the I/O interface 1812 shown in FIG. 21, for example. In some embodiments, blocks 1902 and 1904 may direct the trainer processor 1800 to store representations of the LV EF training records in the location 1840 of the storage memory 1804 shown in FIG. 21.

Referring to FIG. 22, in various embodiments, blocks 1906 to 1912 may be executed to train or update the parameters defining a neural network function stored in the location 1842 of the storage memory 1804, which may in various embodiments have architecture generally similar to the neural network function 1440 shown in FIG. 19.

In some embodiments, in order to train the neural network function, loss defined as follows may be minimized or reduced:

$$l_{total} = l_{reg}EF_{i,Simpson's}^{A2C} + l_{reg}EF_{i,Simpson's}^{A4C} + l_{i,Simpson's}^{Biplane} + l_{CCE}EF_{i,Visual}^{Biplane}$$

where the $l_{CCE}EF_{i,Visual}^{Biplane}$ may be determined generally as discussed herein regarding quality assessment, as follows:

$$l_{CCE}EF_{i,Visual}^{Biplane} = -\frac{1}{|D|}\sum_{i=1}^{D}(\log p(a_i \mid x_i, W))$$

and where $l_{reg}EF_{i,Simpson's}^{A2C}$, $l_{reg}EF_{i,Simpson's}^{A4C}$, and $l_{reg}EF_{i,Simpson's}^{Biplane}$ may be determined using a loss function as follows:

$$l_{reg} = \frac{1}{|D|}\sum_{i=1}^{D}(y_i - \hat{y}_i)^2$$

where $y_i$ and $\hat{y}_i$ are the true and predicted numerical label, respectively. This may be called the norm-2 (Euclidean loss) which is used for regression (hence $l_{reg}$).

Accordingly, referring to FIG. 22, blocks 1906-1912 may be executed to determine $\log p(a_i \uparrow x_i, W))$ for each input $x_i$.

Block 1906 directs the trainer processor 1800 to consider a set of training images as a subject set of training images. For example, in some embodiments, block 1906 may direct the trainer processor 1800 to consider the training images included in the LV EF training record 2000 shown in FIG. 23 to be the subject set of training images.

Block 1908 directs the trainer processor 1800 to, for the subject set of training images, cause the at least one neural network function to be applied to the set of training images to determine at least one property confidence distribution parameter.

For example, in some embodiments, block 1908 may direct the trainer processor 1800 to input the training images from the fields 2004 and 2006 of the LV EF training record 2000 into the neural network function stored in the location 1842 of the storage memory 1804, which has architecture generally similar to that shown at 1440 in FIG. 19, to cause a visual assessment LV EF mean and standard deviation to be determined. In some embodiments, block 1908 may direct the trainer processor 1800 to store the visual assessment LV EF mean and standard deviation in the locations 1844 and 1846 of the storage memory 1804 shown in FIG. 21.

In some embodiments, block 1908 may concurrently cause LV EF means and standard deviations to be determined for each of A2C Simpson's, A4C Simpson's, and Biplane Simpson's methods, using the neural network function. In some embodiments, block 1908 may direct the trainer processor 1800 to store each of the numerical mean and standard deviations determined in the location 1848 of the storage memory 1804, each associated with a method type identifier (e.g., "A2C Simpson's", "A4C Simpson's" or "Biplane Simpson's") and a session identifier.

Block 1910 then directs the trainer processor to cause a cumulative distribution function defined at least in part by the at least one property confidence distribution parameter to be applied to a range associated with the expert evaluation property associated with the set of images, to determine a property confidence representing a confidence that the set of images should be associated with the expert evaluation property. In some embodiments, block 1910 may direct the trainer processor to read the visual assessment from the visual assessment LV EF field 2008 and to apply a Gaussian cumulative distribution function based on a range associated with the visual assessment. For example, in some embodiments, visual assessments of "Severe dysfunction", "Moderate dysfunction", "Mild dysfunction", and "Normal function", may be associated with ranges of [0.0–0.20], (0.20–0.40], (0.40–0.55], and (0.55–0.80), respectively. This information may have been previously provided and stored in the location 1840 of the storage memory 1804, for example.

In various embodiments, where the visual assessment LV EF field 2008 stores "Normal function", block 1910 may direct the trainer processor to use a range of (0.55–0.80] in the Gaussian cumulative distribution function. In various embodiments, block 1910 may direct the trainer processor to normalize the result to determine a property confidence.

In various embodiments, block 1910 may direct the trainer processor 1800 to store the determined property confidence in the location 1850 of the storage memory 1804. In some embodiments, block 1910 may direct the trainer processor 1800 to store the determined confidence in association with the set of training images from which it was determined. For example, in some embodiments, block 1910 may direct the trainer processor to store a training confidence record 2040 as shown in FIG. 24 in the location 1850 of the storage memory 1804. Referring to FIG. 24, the training confidence record 2040 includes a session identifier field 2042 for associating the confidence with a session and a confidence field 2044 for storing the determined confidence.

In various embodiments, after execution of block 1910, block 1912 may direct the trainer processor 1800 to determine whether there are any additional training images to be considered. For example, in some embodiments, block 1912 may direct the trainer processor 1800 to determine whether all of the sets of training images received at block 1902 have been considered. If at block 1912, it is determined that additional training images are to be considered, the trainer processor 1800 is directed to return to block 1906 and consider another set of training images as the subject set of training images. Blocks 1908 and 1910 are then executed with the new subject set of training images.

If at block 1912 it is determined that no further training images are to be considered, block 1912 directs the trainer processor to proceed to block 1914. In various embodiments, when the trainer processor 1800 proceeds to block 1914, there may be stored in the location 1850 of the storage memory 1804 numerous training confidence records having format generally similar to the training confidence record 2040 shown in FIG. 24.

Block 1914 then directs the trainer processor 1800 to cause the at least one neural network function to be updated to reduce a loss, the loss determined based at least in part on the determined property confidences. In some embodiments, block 1914 may direct the trainer processor 1800 to train the neural network function by reducing or minimizing a loss defined as follows:

$$l_{total} = l_{reg}EF_{i,Simpson's}^{A2C} + l_{reg}EF_{i,Simpson's}^{A4C} + l_{reg}EF_{i,Simpson's}^{Biplane} + l_{CCE}EF_{i,Visual}^{Biplane}$$

where the losses are defined as described above.

In some embodiments, after block 1914 has been completed, the trainer processor 1800 may return to block 1906 and the neural network may be further trained. In various embodiments, blocks 1906-1914 may be repeated numerous times to train the neural network function and try to minimize the loss function.

In some embodiments, the neural network function as well as the cumulative distribution function layer may be implemented in Keras with TensorFlow backend. In various embodiments, the images around the ultrasound beam may be automatically cropped and the cine series may be uniformly down-sampled to tensors of dimensions H×W× F=128×128×15 on the fly, where the F frames are sampled uniformly from one full cardiac cycle in each video. In some embodiments, the neural network function may be trained end-to-end from scratch on an Nvidia Tesla GPU. Adaptive moment (Adam) optimization may be used, with the learning rate of α=1e−4, which may have been found experimentally. To account for an imbalanced distribution of samples, for each sample, weights may be assigned inversely proportional to the frequency of the class to which they belonged. In order to prevent model over-fitting, heavy data augmentation may be performed by applying random gamma intensity transformations, rotation, zoom and cropping, on the fly during training. Similarly, in some embodiments, the starting point of the cine series may be selected randomly during training to ensure the invariance of the visual assessment model with respect to cardiac phase. Regularization may be applied on the weight decay.

In various embodiments, alternative or additional neural network training processes may be used. In various embodiments, after blocks 1906-1914 have been executed one or more times, data defining a trained neural network function generally as shown at 1440 in FIG. 19 may be stored in the location 1842 of the storage memory 1804 shown in FIG. 21.

In some embodiments, the flowchart 1900 may include a block for directing the trainer processor 1800 to produce signals representing the trained neural network function for causing a representation of the trained neural network function to be transmitted to the image analyzer 1200 shown in FIG. 17. In some embodiments, the image analyzer 1200 may store the representation of the trained neural network function in the location 1242 of the storage memory 1204.

In various embodiments, the image analyzer 1200 may be configured to execute the flowchart 1400 shown in FIG. 18, generally as described herein, to use the trained neural network function and determine confidences associated with respective visual assessments of LV EF, generally as described herein. In various embodiments, the image analyzer 1200 may be configured to also determine mean and standard deviations for assessments of LV EF for each of A2C Simpson's, Biplane Simpson's and A4C Simpsons, as shown in the neural network function 1440 shown in FIG. 19.

In some embodiments, using a neural network function that trains for the various Simpson's method assessments in addition to the visual assessment of LV EF may facilitate improved accuracy in the training of neural network function and increased accuracy in the determined LV EF assessments. However, in some embodiments, an image analyzer and neural network trainer generally similar to the image analyzer 1200 and neural network trainer 1700 shown in FIGS. 17 and 21 may be configured to function generally as described herein, but with a neural network function that is focussed only on the visual assessment of LV EF. In such embodiments, the portions of the neural network that are not directed to determining visual assessment of LV EF may be omitted. In such embodiments, the loss function that may be minimized may be simply $l_{CCE}EF_{i,Visual}^{Biplane}$.

Various Embodiments

In some embodiments, the cumulative distribution function applied may include non-Gaussian cumulative distribution function, such as, for example, a Laplace cumulative distribution function or gamma distribution function. In such embodiments, the following equations may be used to determine at least one of the property confidences:

$$\hat{p}_c^* = F(u_c) - F(l_c)$$

where $$F(z) = \frac{1}{2}(1 + \text{sgn}(z - f(x)))\left(1 - \exp\left(-\frac{|z - f(x)|}{g(x)}\right)\right)$$

where f(x) is a property confidence distribution parameter that may be determined using the same neural network architecture described herein for determining the mean and g(x) is a property confidence distribution parameter that may be determined using the same neural network described herein for determining the standard deviation. In various embodiments, for the Laplace cumulative distribution function, the property confidence distribution parameters f(x) and g(x) may be a location and a scale parameter respectively for the Laplace cumulative distribution function.

Accordingly, in some embodiments when using the Laplace cumulative distribution function, an absolute difference around mean may be used while the Gaussian cumulative distribution implements a squared difference. In some embodiments, given the same training data, Laplace cumulative distribution function computed probabilities may be more softly or evenly distributed in respective classes than they would be using a Gaussian cumulative distribution function.

In various embodiments, the modification to replace the Gaussian density with the Laplace distribution may happen inside the CDF-Prob layer by editing the F(z) definition. Comparing the numerical values, it may be observed that better performance for some scenarios may be reached using the Gaussian distribution but with other scenarios, the Laplace distribution may provide better performance. In some embodiments, boundary classes, such as "Excellent" and "Poor" may be better approximated using a Gamma cumulative distribution function.

In various embodiments, the choice of cumulative distribution function may depend on the training data. In some embodiments, it may be difficult to predict which of the cumulative distribution functions may work best and so one or more cumulative distribution functions may be used and the results compared. In some embodiments, a particular cumulative distribution function to be used for image analysis may be chosen based on testing the cumulative distribution functions with the training data.

In some embodiments, the cumulative distribution function may be symmetric, such as the Gaussian cumulative distribution function described herein. In some embodiments, the cumulative distribution function may be asymmetric, such as a Gamma cumulative distribution function. In some embodiments, an asymmetric cumulative distribution function or model may better fit the training data than a symmetric cumulative distribution function and/or vice versa. In some embodiments, being able to display results for an asymmetric cumulative distribution function may be important for clinical parameters such as ejection fraction. For example, even if a mean is at a certain point, this may not provide enough information, particularly when the cumulative distribution function is asymmetric. In such embodiments, it may be particularly helpful to display confidences associated with particular ranges and/or representations of the property confidence distribution parameters.

Figure 25:
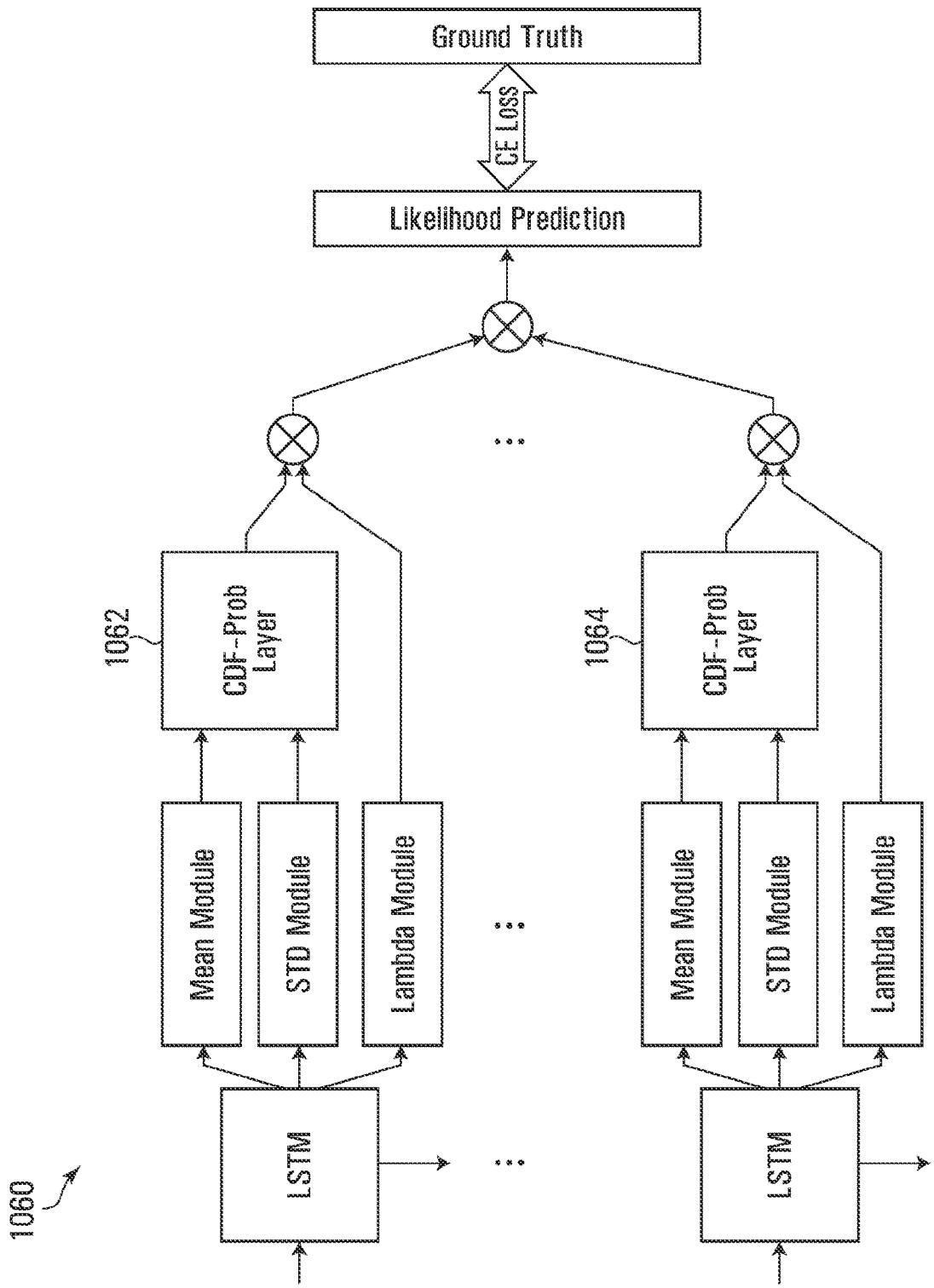
FIG. 25 is a representation of a mixture model that may be included in a neural network function used in the image analyzer and/or neural network trainer shown in FIGS. 3 and 12 in accordance with various embodiments of the present disclosure.

In some embodiments, a mixture model variation may be used wherein a cumulative distribution function may be applied to each of the mean and standard deviation outputs, prior to averaging. For example, referring to FIG. 25, there is shown a 10-component mixture model 1060 from a quality assessment mean and standard deviation neural network function that may be used in accordance with various embodiments. In some embodiments, the model 1060 may replace elements of the neural network functions 300 and 980 shown in FIGS. 5 and 14 respectively from the LSTM forward, for example, such that the same DenseNet may be used. In some embodiments, mean and standard deviation values determined before averaging may be used in respective cumulative distribution functions (e.g., CDF modules 1062 and 1064). In some embodiments, the LSTM features may also be fed to compute an additional value lambda (softmaxed over the 10 steps) to be the weighting parameter for each component determined from the cumulative distribution functions. The weighted CDFs may then be summed to compute the final likelihood distribution which replaces the usage of $$\hat{p}_c = \frac{\hat{p}_c^*}{\sum_{c \in C} \hat{p}_c^*}$$

for training the model. In various embodiments, the learned softmax weighting parameters may share the concept of attention mechanism.

In some embodiments, 10 components may be used because of the 10 time steps, where each step does have mean and standard deviation estimations before the averaging. Hence, in some embodiments, the mixture model architecture may have the "Averaging Mean" and "Averaging STD" modules removed, and the per step mean and standard deviation estimations may be directly plugged to one CDF-Prob module to estimate the property confidences. In various embodiments, using a mixture model may facilitate improved mixing of the confidences or estimations across several consecutive frames.

In some embodiments, a Gaussian mixture model may have more fitting power than just one Gaussian as each Gaussian in the mixture may allow the modelling of a subpopulation. In some embodiments, if the exact distribution has many peaks, one Gaussian may give a worse fitting than a mixture of two Gaussians.

In various embodiments, the ranges associated with the properties may be overlapping or spaced apart. In some embodiments, the ranges associated with the properties may have been previously provided and stored in storage memory.

In some embodiments, each of the sets of training images may have been labeled more than once, for example, by the same or by different medical professionals. In some embodiments, this may help to reduce inter-observer variability. In such embodiments, each set of training images may be associated with more than one property. For example, in some embodiments, each set of training images may be associated with two quality assessments provided by the same medical professional at different times, which may differ because a medical professional may have provided inconsistent labeling. In some embodiments, a system generally similar to the system 700 shown in FIG. 11 may be used to train a quality assessment mean and standard deviation neural network function except that the loss function may be defined as follows:

$$l(W, D) = -\frac{1}{|D|} \sum_{i=1}^{D} (\lambda_1 \log p(a_{1i} | x_i, W) + \lambda_2 \log p(a_{2i} | x_i, W))$$

where $A_1$ is a set of first labels for the sets of images X and $A_2$ is a set of second labels for the sets of images X, as provided by the same medical professional and where $\lambda_1$ and $\lambda_2$ are the weighting assignments for the observed classes respectively. In some embodiments, a soft targets method may be used such that $\lambda_1 = \lambda_2 = \frac{1}{2}$.

In various embodiments, alternative CNN and/or RNN models may be used in place of the DenseNet+LSTM models disclosed herein.

Figure 26:
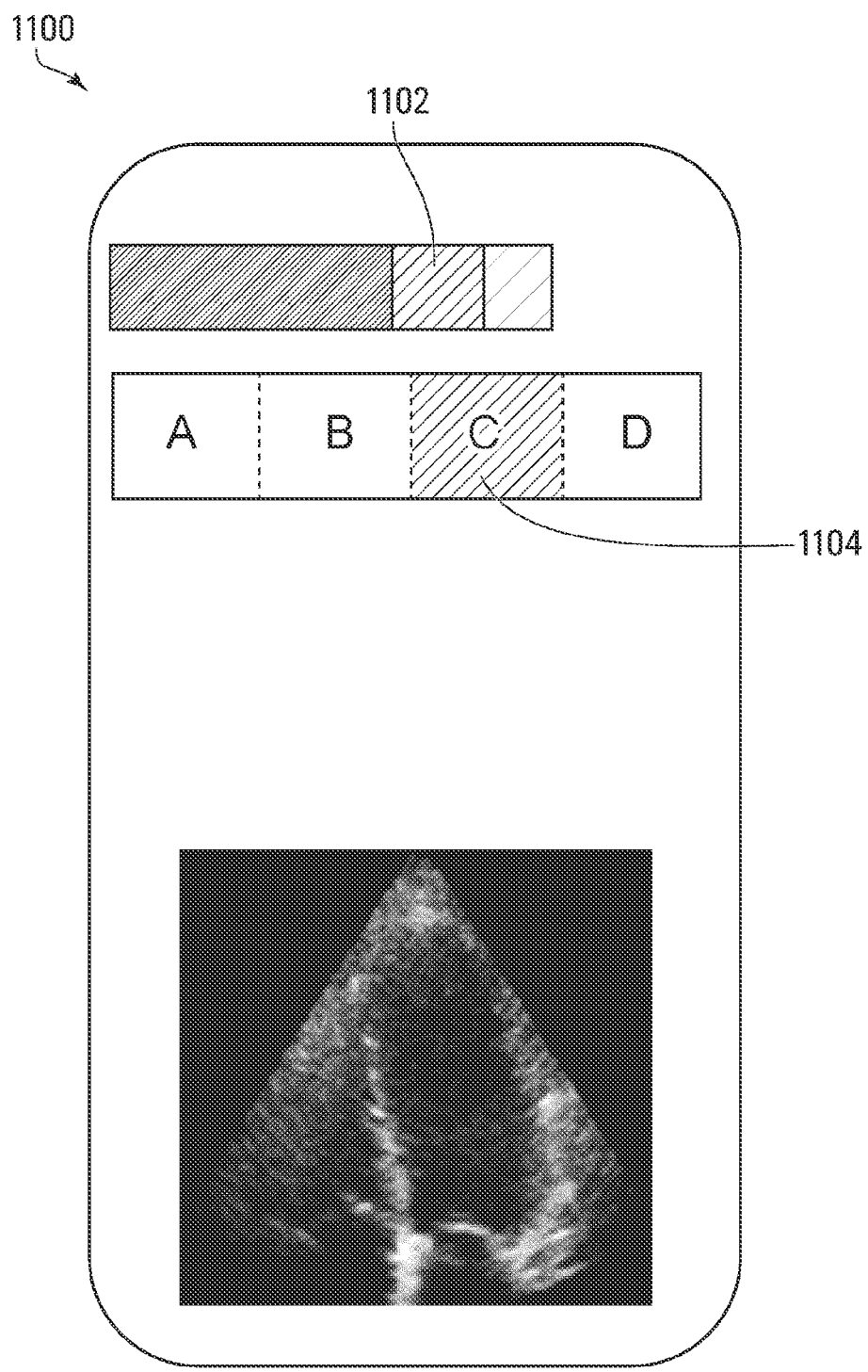
FIG. 26 is a representation of an exemplary display that may be displayed by the system shown in FIG. 2 in accordance with various embodiments of the present disclosure.

In some embodiments, the flowchart 200 may include blocks of code for directing the analyzer processor 100 to produce signals for causing the display 24 to display various representations of information. For example, in some embodiments, the display 24 may display a depiction 1100 as shown in FIG. 26 where both a bar 1102 and a color or shade of the element C 1104 (associated with category C or "Good", for example), may represent the property confidence associated therewith. In some embodiments, the bar 1102 may be omitted.

In some embodiments, a representation of the property confidences may be omitted and only a representation of the mean and standard deviation may be displayed.

In some embodiments, the training data received by the neural network trainer 708 shown in FIGS. 11 and 12 may include images from a plurality of view categories, such as, for example, each type of the 14 standard echocardiography views (A#C: A2C, A3C, A4C, A5C, apical #-chamber view, PLAX: parasternal long axis view, RVIF: right ventricle inflow view, S#C: S4C S5C, subcostal #-chamber view, IVC: subcostal inferior vena cava view, PSAX-A: parasternal short axis view at aortic valve, PSAX-M: PSAX view at mitral annulus valve level, PSAX-PM: PSAX view at mitral valve papillary muscle level, PSAX-APEX: PSAX view at apex level, and SUPRA: suprasternal) and the neural network may be configured to handle all of the views and provide quality assessments for each.

In some embodiments, the neural network trainer 708 and the image analyzer 702 shown in FIG. 11 may be integrated as a single device.

In some embodiments, a system generally similar to the systems described herein may be configured to use a single image as the set of images.

In some embodiments, epistemic and aleatoric confidences may be added together to generate a total confidence. For example, if the confidences are independent and Gaussian, then the total confidence may be determined as:

(Total Confidence)^2=(Aleatoric Confidence)^2+
(Epistemic Confidence)^2

While specific embodiments of the present disclosure have been described and illustrated, such embodiments should be considered illustrative of the present disclosure only and not as limiting the present disclosure as construed in accordance with the accompanying claims.

Selected Embodiments and Claim Concepts

This section describes additional aspects and features of computer-implemented methods for facilitating neural network image analysis, presented without limitation as a series of paragraphs, some or all of which may be alphanumerically designated for clarity and efficiency. Some of the paragraphs below may expressly refer to and further limit other paragraphs, providing examples of suitable combinations.

A0. A computer-implemented method of facilitating neural network image analysis, the method comprising:
receiving signals representing a set of images;
causing at least one neural network function to be applied to the set of images to determine at least one property confidence distribution parameter; and
causing a cumulative distribution function defined at least in part by the at least one property confidence distribution parameter to be applied to a plurality of ranges, each range associated with a respective property that may be associated with the set of images, to determine a plurality of property confidences, each of the property confidences representing a confidence that the set of images should be associated with a respective one of the properties.

A1. The method of A0, wherein the cumulative distribution function includes a Gaussian cumulative distribution function and the at least one property confidence distribution parameter includes a property distribution mean and a property distribution standard deviation.

A2. The method of A0 or A1, wherein the cumulative distribution function includes a Laplace cumulative distribution function and the at least one property confidence distribution parameter includes a location and scale parameter for the Laplace cumulative distribution function.

A3. The method of any one of paragraphs A0 through A2, wherein the set of images includes ultrasound images.

A4. The method of any one of paragraphs A0 through A3, wherein the properties include at least one clinical parameter related to a subject depicted by the set of images.

A5. The method of A4, wherein the properties include echocardiogram estimated ejection fraction function diagnoses.

A6. The method of A4, wherein the properties include a quality assessment of the set of images.

A7. The method of any one of paragraphs A0 through A6, further comprising producing signals for causing at least one display to display a representation of at least one of the property confidences.

A8. The method of A7, further comprising producing signals for causing at least one display to display a representation of the at least one property confidence distribution parameter.

A9. The method of any one of paragraphs A0 through A8, further comprising training the at least one neural network function, the training comprising:
receiving signals representing a plurality of sets of training images;
receiving signals representing expert evaluation properties, each of the expert evaluation properties provided by an expert and associated with one of the sets of training images; and
causing the at least one neural network function to be trained using the sets of training images as respective inputs, wherein causing the at least one neural network function to be trained comprises:
for each of the sets of training images:
causing the at least one neural network function to be applied to the set of training images to determine at least one training property confidence distribution parameter; and
causing a training cumulative distribution function defined at least in part by the at least one training property confidence distribution parameter to be applied to a range associated with the expert evaluation property associated with the set of images, to determine a training property confidence representing a confidence that the set of training images should be associated with the expert evaluation property; and
causing the at least one neural network function to be updated to reduce a loss, the loss determined based at least in part on the determined training property confidences.

B0. A computer-implemented method of training at least one neural network function to facilitate image analysis, the method comprising:
receiving signals representing a plurality of sets of training images;

receiving signals representing expert evaluation properties, each of the expert evaluation properties provided by an expert and associated with one of the sets of training images; and causing the at least one neural network function to be trained using the sets of training images as respective inputs, wherein causing the at least one neural network function to be trained comprises:
  for each of the sets of training images:
    causing the at least one neural network function to be applied to the set of training images to determine at least one property confidence distribution parameter; and
    causing a cumulative distribution function defined at least in part by the at least one property confidence distribution parameter to be applied to a range associated with the expert evaluation property associated with the set of images, to determine a property confidence representing a confidence that the set of training images should be associated with the expert evaluation property; and
  causing the at least one neural network function to be updated to reduce a loss, the loss determined based at least in part on the determined property confidences.

B1. The method of B0, wherein the cumulative distribution function includes a Gaussian cumulative distribution function and the at least one property confidence distribution parameter includes a property distribution mean and a property distribution standard deviation.

B2. The method of B0 or B1, wherein the cumulative distribution function includes a Laplace cumulative distribution function and the at least one property confidence distribution parameter includes a location and scale parameter for the Laplace cumulative distribution function.

B3. The method of any one of paragraphs B0 through B2, wherein the set of images includes ultrasound images.

B4. The method of any one of paragraphs B0 through B3, wherein the properties include at least one clinical parameter related to a subject depicted by the set of images.

B5. The method of B4 wherein the properties include echocardiogram estimated ejection fraction function diagnoses.

B6. The method of B4 wherein the properties include a quality assessment of the set of images.

C0. A system for facilitating ultrasonic image analysis comprising at least one processor configured to perform the method of any one of paragraphs A0 through A9 or B0 through B6.

D0. A non-transitory computer readable medium having stored thereon codes which when executed by at least one processor cause the at least one processor to perform the method of any one of paragraphs A0 through A9 or B0 through B6.

E0. A system for facilitating neural network image analysis, the system comprising:
  means for receiving signals representing a set of images;
  means for causing at least one neural network function to be applied to the set of images to determine at least one property confidence distribution parameter; and
  means for causing a cumulative distribution function defined at least in part by the at least one property confidence distribution parameter to be applied to a plurality of ranges, each range associated with a respective property that may be associated with the set of images, to determine a plurality of property confidences, each of the property confidences representing a confidence that the set of images should be associated with a respective one of the properties.

F0. A system for training at least one neural network function to facilitate image analysis, the system comprising:
  means for receiving signals representing a plurality of sets of training images;
  means for receiving signals representing expert evaluation properties, each of the expert evaluation properties provided by an expert and associated with one of the sets of training images; and
  means for causing the at least one neural network function to be trained using the sets of training images as respective inputs, wherein the means for causing the at least one neural network function to be trained comprises:
    means for, for each of the sets of training images:
      causing the at least one neural network function to be applied to the set of training images to determine at least one property confidence distribution parameter; and
      causing a cumulative distribution function defined at least in part by the at least one property confidence distribution parameter to be applied to a range associated with the expert evaluation property associated with the set of images, to determine a property confidence representing a confidence that the set of training images should be associated with the expert evaluation property; and
    means for causing the at least one neural network function to be updated to reduce a loss, the loss determined based at least in part on the determined property confidences.

CONCLUSION

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only. The subject matter of the disclosure includes all novel and nonobvious combinations and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

The invention claimed is:

1. A computer-implemented method of facilitating neural network image analysis, the method comprising:
  receiving signals representing a set of images;
  causing at least one neural network function to be applied to the set of images to determine at least one property confidence distribution parameter; and
  causing a cumulative distribution function defined at least in part by the at least one property confidence distribution parameter to be applied to a plurality of ranges, each range associated with a respective property that is capable of being associated with the set of images, to determine a plurality of property confidences, each of the property confidences representing a confidence that the set of images is associated with a respective one of the properties.

2. The method of claim 1 wherein the cumulative distribution function includes a Gaussian cumulative distribution function and the at least one property confidence distribution parameter includes a property distribution mean and a property distribution standard deviation.

3. The method of claim 1 wherein the cumulative distribution function includes a Laplace cumulative distribution function and the at least one property confidence distribution parameter includes a location and scale parameter for the Laplace cumulative distribution function.

4. The method of claim 1 wherein the set of images includes ultrasound images.

5. The method of claim 1 wherein the properties include at least one clinical parameter related to a subject depicted by the set of images.

6. The method of claim 5 wherein the properties include echocardiogram estimated ejection fraction function diagnoses.

7. The method of claim 5 wherein the properties include a quality assessment of the set of images.

8. The method of claim 1 further comprising producing signals for causing at least one display to display a representation of at least one of the property confidences.

9. The method of claim 8 further comprising producing signals for causing at least one display to display a representation of the at least one property confidence distribution parameter.

10. The method of claim 1 further comprising training the at least one neural network function, the training comprising:
   receiving signals representing a plurality of sets of training images;
   receiving signals representing expert evaluation properties, each of the expert evaluation properties provided by an expert and associated with one of the sets of training images; and
   causing the at least one neural network function to be trained using the sets of training images as respective inputs, wherein causing the at least one neural network function to be trained comprises:
      for each of the sets of training images:
         causing the at least one neural network function to be applied to the set of training images to determine at least one training property confidence distribution parameter; and
         causing a training cumulative distribution function defined at least in part by the at least one training property confidence distribution parameter to be applied to a range associated with the expert evaluation property associated with the set of images, to determine a training property confidence representing a confidence that the set of training images should be associated with the expert evaluation property; and
      causing the at least one neural network function to be updated to reduce a loss, the loss determined based at least in part on the determined training property confidences.

11. A computer-implemented method of training at least one neural network function to facilitate image analysis, the method comprising:
   receiving signals representing a plurality of sets of training images;
   receiving signals representing expert evaluation properties, each of the expert evaluation properties provided by an expert and associated with one of the sets of training images; and
   causing the at least one neural network function to be trained using the sets of training images as respective inputs, wherein causing the at least one neural network function to be trained comprises:
      for each of the sets of training images:
         causing the at least one neural network function to be applied to the set of training images to determine at least one property confidence distribution parameter; and
         causing a cumulative distribution function defined at least in part by the at least one property confidence distribution parameter to be applied to a range associated with the expert evaluation property associated with the set of images, to determine a property confidence representing a confidence that the set of training images is associated with the expert evaluation property; and
      causing the at least one neural network function to be updated to reduce a loss, the loss determined based at least in part on the determined property confidences.

12. The method of claim 11 wherein the cumulative distribution function includes a Gaussian cumulative distribution function and the at least one property confidence distribution parameter includes a property distribution mean and a property distribution standard deviation.

13. The method of claim 11 wherein the cumulative distribution function includes a Laplace cumulative distribution function and the at least one property confidence distribution parameter includes a location and scale parameter for the Laplace cumulative distribution function.

14. The method of claim 11 wherein the set of images includes ultrasound images.

15. The method of claim 11 wherein the properties include at least one clinical parameter related to a subject depicted by the set of images.

16. The method of claim 15 wherein the properties include echocardiogram estimated ejection fraction function diagnoses.

17. The method of claim 15 wherein the properties include a quality assessment of the set of images.

18. A system for facilitating ultrasonic image analysis, the system comprising at least one processor configured to:
   receive signals representing a set of images;
   cause at least one neural network function to be applied to the set of images to determine at least one property confidence distribution parameter; and
   cause a cumulative distribution function defined at least in part by the at least one property confidence distribution parameter to be applied to a plurality of ranges, each range associated with a respective property that is capable of being associated with the set of images, to determine a plurality of property confidences, each of the property confidences representing a confidence that the set of images is associated with a respective one of the properties.

19. A non-transitory computer readable medium having stored thereon codes which when executed by at least one processor cause the at least one processor to:
   receive signals representing a set of images;
   cause at least one neural network function to be applied to the set of images to determine at least one property confidence distribution parameter; and
   cause a cumulative distribution function defined at least in part by the at least one property confidence distribution parameter to be applied to a plurality of ranges, each range associated with a respective property that is capable of being associated with the set of images, to determine a plurality of property confidences, each of the property confidences representing a confidence that the set of images is associated with a respective one of the properties.

20. A system for facilitating neural network image analysis, the system comprising:
- means for receiving signals representing a set of images;
- means for causing at least one neural network function to be applied to the set of images to determine at least one property confidence distribution parameter; and
- means for causing a cumulative distribution function defined at least in part by the at least one property confidence distribution parameter to be applied to a plurality of ranges, each range associated with a respective property that is capable of being associated with the set of images, to determine a plurality of property confidences, each of the property confidences representing a confidence that the set of images is associated with a respective one of the properties.

21. A system for training at least one neural network function to facilitate image analysis, the system comprising:
- means for receiving signals representing a plurality of sets of training images;
- means for receiving signals representing expert evaluation properties, each of the expert evaluation properties provided by an expert and associated with one of the sets of training images; and
- means for causing the at least one neural network function to be trained using the sets of training images as respective inputs, wherein the means for causing the at least one neural network function to be trained comprises:
  - means for, for each of the sets of training images:
    - causing the at least one neural network function to be applied to the set of training images to determine at least one property confidence distribution parameter; and
    - causing a cumulative distribution function defined at least in part by the at least one property confidence distribution parameter to be applied to a range associated with the expert evaluation property associated with the set of images, to determine a property confidence representing a confidence that the set of training images is associated with the expert evaluation property; and
  - means for causing the at least one neural network function to be updated to reduce a loss, the loss determined based at least in part on the determined property confidences.

* * * * *